United States Patent
Blackley et al.

(10) Patent No.: US 11,393,568 B2
(45) Date of Patent: Jul. 19, 2022

(54) BLOCKCHAIN PRESCRIPTION MANAGEMENT SYSTEM

(71) Applicant: PRESCRYPTIVE HEALTH, INC., Redmond, WA (US)

(72) Inventors: Christopher Scott Blackley, Redmond, WA (US); David Allen Smith, Kirkland, WA (US); John Marley Gray, Bellevue, WA (US); Rhetick Sengupta, Seattle, WA (US); Kevin C. Young, Redmond, WA (US)

(73) Assignee: PRESCRYPTIVE HEALTH, INC., Redmond, WA (US)

( * ) Notice: Subject to any disclaimer, the term of this patent is extended or adjusted under 35 U.S.C. 154(b) by 658 days.

(21) Appl. No.: 15/855,930

(22) Filed: Dec. 27, 2017

(65) Prior Publication Data
US 2019/0198144 A1    Jun. 27, 2019

(51) Int. Cl.
| | |
|---|---|
| G16H 20/10 | (2018.01) |
| H04L 9/08 | (2006.01) |
| G06F 16/27 | (2019.01) |
| G06F 16/182 | (2019.01) |
| H04L 9/32 | (2006.01) |

(52) U.S. Cl.
CPC .......... *G16H 20/10* (2018.01); *G06F 16/182* (2019.01); *G06F 16/27* (2019.01); *H04L 9/0861* (2013.01); *H04L 9/3239* (2013.01); *H04L 9/3247* (2013.01); *H04L 2209/38* (2013.01); *H04L 2209/56* (2013.01)

(58) Field of Classification Search
CPC combination set(s) only.
See application file for complete search history.

(56) References Cited

U.S. PATENT DOCUMENTS

2005/0240305 A1    10/2005    Bogash et al.
2009/0198520 A1*   8/2009    Piovanetti-Perez
(Continued)

FOREIGN PATENT DOCUMENTS

WO    2019133546 A1    7/2019

OTHER PUBLICATIONS

International Search Report and Written Opinion received in the Application No. PCT/US2018/67383, dated Apr. 30, 2019, 11 pages.

*Primary Examiner* — Michael Tomaszewski
*Assistant Examiner* — William T. Monticello
(74) *Attorney, Agent, or Firm* — Davis Wright Tremaine LLP

(57) ABSTRACT

A system for managing prescriptions via a blockchain is provided. The system records in the blockchain a prescription transaction that identifies a prescription that has been written for a patient. The system then records in the blockchain a submission selection transaction with code for controlling selection of a pharmacy to dispense the prescription. For pharmacies that provide a submission for dispensing the prescription, the system records in the blockchain a submission transaction with submission information relating to dispensing of the prescription by the pharmacy. When a pharmacy is selected to dispense the prescription, the system records in the blockchain a selected submission transaction indicating the pharmacy selected to dispense the prescription. When the prescription is dispensed, the system records in the blockchain a dispense transaction indicating that the selected pharmacy has dispensed the prescription.

25 Claims, 15 Drawing Sheets

(56) References Cited

U.S. PATENT DOCUMENTS

| | | |
|---|---|---|
| 2012/0253846 A1* | 10/2012 | John et al. |
| 2014/0114472 A1 | 4/2014 | Bossi et al. |
| 2015/0332283 A1 | 11/2015 | Witchey |
| 2017/0132393 A1 | 5/2017 | Natarajan et al. |
| 2017/0262594 A1* | 9/2017 | Janin et al. |
| 2017/0364655 A1 | 12/2017 | Farooqi |
| 2018/0130050 A1* | 5/2018 | Taylor et al. |
| 2018/0253682 A1* | 9/2018 | Gilman et al. |
| 2019/0057763 A1* | 2/2019 | Stockert et al. |
| 2019/0156938 A1* | 5/2019 | Brunner |
| 2019/0180291 A1* | 6/2019 | Schmeling et al. |

* cited by examiner

200

| select medicine | | |
|---|---|---|
| 201 prescribe medicine information | | |
| alternatives | price | incentive |
| 202 drug xyz | $10 | waive co-pay |
| drug abc | $20 | 20% off |
| ⋮ | | |

| select pharmacy | | |
|---|---|---|
| 211 prescription information | | |
| pharmacy | price | incentive |
| acme | $20 | 15% store coupon |
| 212 xyz | $25 | 25% off next refill |
| abc | $35 | next refill free |
| ⋮ | | |

*FIG. 2B*

220 report dose taken 221 select prescription [▼]

222 select quantity [▼]

223 when taken    date    time 224 submit

*FIG. 2C*

230 report outcome 231 condition [▼]

232 outcome [▼]

233 when    date    time 234 submit

*FIG. 2D*

BLOCKCHAIN PRESCRIPTION MANAGEMENT SYSTEM

BACKGROUND

The bitcoin system was developed to allow electronic cash to be transferred directly from one party to another without going through a financial institution, as described in the white paper entitled "Bitcoin: A Peer-To-Peer Electronic Cash System" by Satoshi Nakamoto. A bitcoin (e.g., an electronic coin) is represented by a chain of transactions that transfers ownership from one party to another party. To transfer ownership of a bitcoin, a new transaction is generated and added to a stack of transactions in a block. The new transaction, which includes the public key of the new owner, is digitally signed by the owner with the owner's private key to transfer ownership to the new owner as represented by the new owner public key. Once the block is full, the block is "capped" with a block header that is a hash digest of all the transaction identifiers within the block. The block header is recorded as the first transaction in the next block in the chain, creating a mathematical hierarchy called a "blockchain." To verify the current owner, the blockchain of transactions can be followed to verify each transaction from the first transaction to the last transaction. The new owner need only have the private key that matches the public key of the transaction that transferred the bitcoin. The blockchain creates a mathematical proof of ownership in an entity represented by a security identity (e.g., a public key), which in the case of the bitcoin system is pseudo-anonymous.

To ensure that a previous owner of a bitcoin did not double-spend the bitcoin (i.e., transfer ownership of the same bitcoin to two parties), the bitcoin system maintains a distributed ledger of transactions. With the distributed ledger, a ledger of all the transactions for a bitcoin is stored redundantly at multiple nodes (i.e., computers) of a blockchain network. The ledger at each node is stored as a blockchain. In a blockchain, the transactions are stored in the order that the transactions are received by the nodes. Each node in the blockchain network may have a complete replica of the entire blockchain. The bitcoin system also implements techniques to ensure that each node will store the identical blockchain even though nodes may receive transactions in different orderings. To verify that the transactions in a ledger stored at a node are correct, the blocks in the blockchain can be accessed from oldest to newest, generating a new hash of the block and comparing the new hash to the hash generated when the block was created. If the hashes are the same, then the transactions in the block are verified. The bitcoin system also implements techniques to ensure that it would be infeasible to change a transaction and regenerate the blockchain by employing a computationally expensive technique to generate a nonce that is added to the block when it is created.

Although the bitcoin system has been very successful, it is limited to transactions in bitcoins or other cryptocurrencies. Efforts are currently underway to use blockchains to support transactions of any type, such as those relating to the sale of vehicles, sale of financial derivatives, sale of stock, payments on contracts, and so on. Such transactions use identity tokens, which are also referred to as digital bearer bonds, to uniquely identify something that can be owned or can own other things. An identity token for a physical or digital asset is generated using a cryptographic one-way hash of information that uniquely identifies the asset. Tokens also have an owner that uses an additional public/private key pair. The owner public key is set as the token owner identity, and when performing actions against tokens, ownership proof is established by providing a signature generated by the owner private key and validated against the public key listed as the owner of the token. A person can be uniquely identified, for example, using a combination of a user name, social security number, and biometric (e.g., fingerprint). A product (e.g., refrigerator) can be uniquely identified, for example, using the name of its manufacturer and its serial number. The identity tokens for each would be a cryptographic one-way hash of such combinations. The identity token for an entity (e.g., person or company) may be the public key of a public/private key pair, where the private key is held by the entity. Identity tokens can be used to identify people, institutions, commodities, contracts, computer code, equities, derivatives, bonds, insurance, loans, documents, and so on. Identity tokens can also be used to identify collections of assets. An identity token for a collection may be a cryptographic one-way hash of the digital tokens of the assets in the collection. The creation of an identity token for an asset in a blockchain establishes provenance of the asset, and the identity token can be used in transactions (e.g., buying, selling, insuring) of the asset stored in a blockchain, creating a full audit trail of the transactions.

To record a simple transaction in a blockchain, each party and asset involved with the transaction needs an account that is identified by a digital token. For example, when one person wants to transfer a car to another person, the current owner and next owner create accounts, and the current owner also creates an account that is uniquely identified by its vehicle identification number. The account for the car identifies the current owner. The current owner creates a transaction against the account for the car that indicates that the transaction is a transfer of ownership transfer, indicates the public keys (i.e., identity tokens) of the current owner and the next owner, and indicates the identity token of the car. The transaction is signed by the private key of the current owner. The transaction is evidence that the next owner is now the current owner.

To enable more complex transactions, some systems use "smart contracts." A smart contract is computer code that implements transactions of a contract or, more generally, behavior of transactions specified by one or more parties. The computer code may be executed in a secure platform (e.g., an Ethereum platform) that supports recording transactions in blockchains. In addition, the smart contract itself is recorded as a transaction in the blockchain using an identity token that is a hash (i.e., identity token) of the computer code so that the computer code that is executed can be authenticated. When deployed, a constructor of the smart contract executes initializing the smart contract and its state. The state of a smart contract is stored persistently in the blockchain. When a transaction is recorded against a smart contract, a message is sent to the smart contract and the computer code of the smart contract executes to implement the transaction (e.g., debit a certain amount from the balance of an account). The computer code ensures that all the terms of the contract are complied with before the transaction is recorded in the blockchain. For example, a smart contract may support the sale of an asset. The inputs to a smart contract to sell a car may be the identity tokens of the seller, the buyer, and the car and the sale price in U.S. dollars. The computer code ensures that the seller is the current owner of the car and that the buyer has sufficient funds in their account. The computer code then records a transaction that transfers the ownership of the car to the buyer and a transaction that transfers the sale price from the buyer's account to the seller's account.

Some efforts have been made by the healthcare industry to use blockchains for storing medical records of patients. For example, the medical records for a patient may be recorded in a blockchain and encrypted with a public key and signed using a private key of the patient. The medical records need to be stored in a way that preserves their privacy. The privacy of medical records may be mandated by a controlling jurisdiction's laws and regulations, such as the Health Insurance Portability and Accountability Act ("HIPAA") of the United States.

Although the actual medical records could be stored in a blockchain, the blockchain may store only portions of the medical records of a patient along with identifiers to one or more repositories that store the remainder of the medical records. For example, since each image (e.g., an x-ray) may be megabytes in size, such images may be stored in an image repository. The blockchain may contain a transaction for each image that contains the identifier of the repository that stores the image along with a hash of the image. When the identified image is accessed, a hash of the image is generated and compared to the hash stored in the blockchain. If the hashes match, then the image is verified as being the actual image, that is, as not having been modified. More complex medical records may be represented in a transaction using a Merkle tree, which is a binary hash tree of hashes generated from the components of the medical records such as images, test results, psychiatric evaluations, family medical history, demographic information, and so on. To generate the Merkle tree for a transaction, a leaf node is generated for each component of the medical record that includes a hash of that component. Nodes with a zero hash value may be generated to ensure that the hash tree is binary. The next higher-level nodes of the Merkle tree are generated to include a hash of the hashes of a pair of leaf nodes. The process continues at successively higher levels until the root node is generated that includes the overall hash of the medical records.

Current attempts to store medical records via a blockchain generally focus on recording what are essentially copies of current medical records in the blockchain. Such current medical records, however, are in some cases not sufficiently detailed to provide a complete medical history of a patient. For example, when a physician writes a prescription, the medical record includes information about the prescription (e.g., drug, dosage, and number of refills). Many patients, however, do not actually have the prescription dispensed or filled, which is referred to as prescription abandonment. For example, when a patient goes to a pharmacy, the patient may find that their insurance will not cover the price of the prescription and that the price is unaffordable for the patient. Even if a prescription is dispensed to a patient, the patient may fail to take the drug as prescribed or even fail to take the drug at all. The medical records typically do not include information on such prescription abandonment or failure to take a drug as prescribed. Moreover, even if such information were to be included in a medical record, the outcomes of taking the drugs as prescribed are often not included in the medical record.

A patient may have medical insurance that is provided by a sponsor such as the patient's employer, a governmental entity, and so on. To help control costs and improve medical outcomes, such a sponsor may define a formulary, which lists the medicines covered by medical insurance. A formulary may specify the medicines and dosages that are approved for the treatment of each disease (or, more generally, condition), including "off-label" uses. A formulary may also specify, for a disease, the order in which medicines are approved to be prescribed. For example, the formulary may specify that drug A needs to be prescribed before drug B can be prescribed. Because the creating and maintaining of a formulary can be expensive, sponsors often rely on pharmacy benefit managers ("PBMs") that provide computer systems to manage formularies, to pay pharmacies, and to receive payment from sponsors. Manufacturers of drugs often provide "incentives" to a PBM so that their drugs will be included in the formularies specified by the PBM and accessible by the computer systems of the PBM. As such, a drug may be included in a formulary in part because of the incentives, rather than based solely on the expected clinical outcome. In addition, a PBM may represent many sponsors and use that leverage to deny pharmacies access to their computer systems, thus effectively preventing the pharmacies from dispensing to employees or participants of the sponsors.

BRIEF DESCRIPTION OF THE DRAWINGS

FIGS. 2A-2D illustrate display pages of a BCPM application in some embodiments.

DETAILED DESCRIPTION

Figure 1:
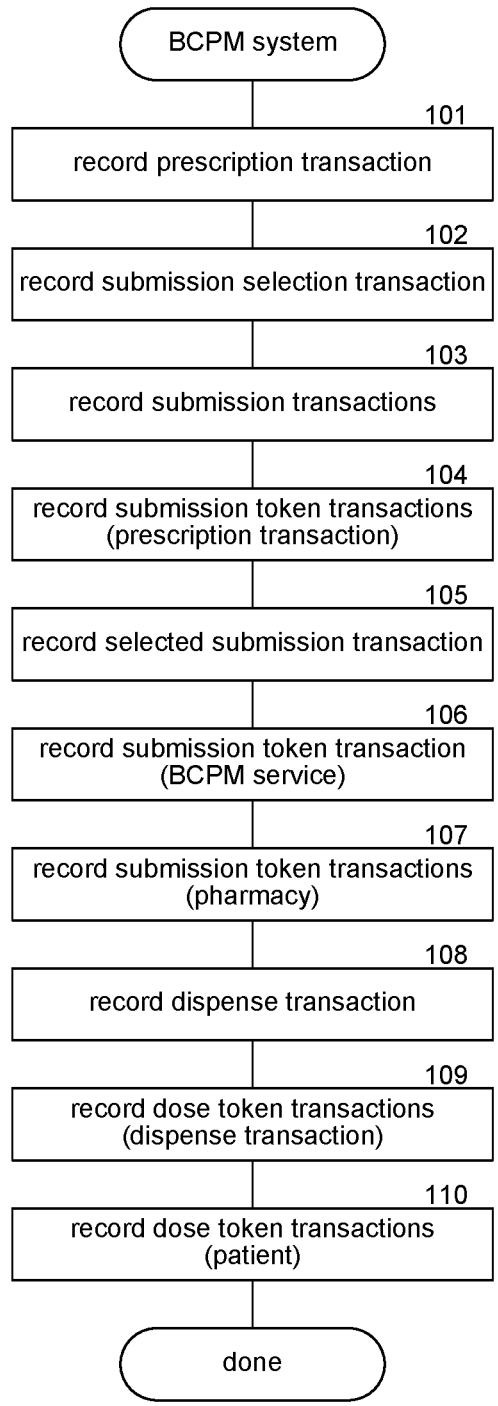
FIG. 1 is a flow diagram that illustrates the overall processing of a BCPM system in some embodiments.

Methods and systems are provided for managing the overall prescription process using a blockchain to track prescriptions, the selection of pharmacies to dispense prescriptions, the dispensing of prescriptions, and the taking of doses by patients. In some embodiments, a blockchain prescription management ("BCPM") system is provided that records in a blockchain (or more generally a distributed ledger) transactions that relate to the prescribing, dispensing, and taking of medicine. When a prescriber (e.g., physician) writes a prescription for a patient, the prescriber may have the prescription entered into an existing prescription system that may be augmented to interface with the BCPM system. The BCPM system records in a blockchain (e.g., a prescription blockchain dedicated to supporting the BCPM system) a corresponding prescription transaction. The prescription transaction includes details of the prescription such as the prescriber, patient, medicine, dose, instructions, and so on. The prescription transaction may include computer code for responding to messages sent to the prescription transaction. For example, the computer code may be part of a smart contract for a prescription transaction.

In some embodiments, at the time the prescription transaction is recorded in the blockchain, the BCPM system may identify alternatives to the prescribed medicine. For example, the BCPM system may access formulary information for a sponsor of the insurance for the patient to identify alternative medicines that are lower-cost than the prescribed medicine, more effective than the prescribed medicine, and so on. The BCPM system may record in the blockchain an alternative medicine transaction that lists the identified alternative medicines and references the prescription transaction. The sponsor of the insurance for the patient or the drug manufacturer may also provide incentives to the patient, such as waiving any copayment or providing a rebate, for selecting certain alternative medicines. The BCPM system may then send information on the alternative medicine to a BCPM application running on a device (e.g., smartphone) of the patient. For example, the BCPM application may be provided with an identifier of the alternative medicine transaction and/or the prescription transaction. The BCPM application displays alternative medicine information to the patient. After the patient (e.g., in consultation with the prescriber) selects a medicine (i.e., the prescribed or an alternative medicine), the BCPM system may record in the blockchain a selected alternative transaction that identifies the selected alternative medicine (if any) and new prescription transaction to override the original prescription transaction.

After the alternative medicines (if any) are presented to the patient, the BCPM system may identify pharmacies that are available to dispense the prescription to the patient. For example, the identified pharmacies may include pharmacies that are geographically close to the current location of the patient, that have previously dispensed prescriptions to the patient, that are approved by a sponsor of the insurance for the patient, and so on. The BCPM system may also collect submission information describing terms on which each pharmacy is willing to dispense the prescription. For example, the terms for a pharmacy may include the copayment amount that the patient will be required to pay, any incentive provided by the pharmacy (e.g., a 25% off in-store coupon), the pickup or delivery date and time for the prescription, and so on. The BCPM system records in the blockchain a submission transaction for each pharmacy that specifies the submission information and directly or indirectly references the prescription transaction. Once the submission transactions are recorded, the BCPM system may send the submission information to the BCPM application running on a device (e.g., smartphone) of the patient. For example, the BCPM application may be provided with an identifier of the prescription transaction, the identifiers of the submission transactions, and/or the submission information. The BCPM application displays the submission information to the patient. After the patient selects a pharmacy, the BCPM system may record in the blockchain a selected submission transaction that identifies the selected pharmacy. The BCPM system may also automatically notify the selected pharmacy. If the patient decides not to select a pharmacy (e.g., because its prices are too high), the patient can discuss options with the prescriber for alternative medicines or pharmacies. The BCPM system thus allows the prescriber and patient to discuss options in real time to identify an appropriate medicine, dosage, pharmacy, and so on that will increase the chances of having a prescription dispensed and reduce the chances of an abandonment.

In some embodiments, when a pharmacy dispenses a prescription, the pharmacy may enter details of the dispensing into an existing pharmacy system that may be augmented to interface with the BCPM system. When the details of the dispensing are entered, the BCPM system may record in the blockchain a dispense transaction. The BCPM system may also record in the blockchain, for each dose of the prescription, a dose token transaction that creates a dose token that is "owned" by the dispense transaction or some other entity (e.g., third party) as the output of the dose token transaction. Alternatively, dose token transactions may be recorded in the blockchain when a dose is manufactured with the manufacturer as the owner. As a dose travels through the supply chain, the ownership of its corresponding dose token changed until it is owned by a pharmacy. When a prescription that includes such a dose is dispensed, ownership of the corresponding dose token may be changed to the dispense transaction. To help identify the dose token corresponding to a dose, each dose may be associated with a unique code. The code may be transmitted to the BCPM system at time of dispense by a pharmacist manually entering the code or scanning a Quick-Response code, by the dose transmitting its code using near-field communications or via a radio-frequency identifier tag, and so on. "Ownership" as used herein does not necessarily mean legal ownership, but rather may be used to refer to states of a token as identified by the current owner. For example, a dose token may be owned by a dispense transaction until the corresponding dose is taken by the patient. When the dose is taken, "ownership" of the dose token is transferred to the patient. A patient may also use the BCPM application to report that a dose has been taken. In response, the BCPM application may record in the blockchain a dose token transaction that inputs a dose token owned by the dispense transaction and outputs a dose token that is owned by the patient. The input dose token would then be considered to be a spent transaction output. The reporting that a dose has been taken may also be performed automatically by electronic circuitry associated with a dose. For example, an ingested capsule may include electronic circuitry that is activated to report when the capsule is dissolved after being ingested. As another example, an administering device (e.g., syringe) may have electronic circuitry that is activated to report when the medicine is mixed with blood.

In some embodiments, the BCPM system may track outcomes of taking a prescription as reported by patients. The BCPM application may provide a display through which a patient can specify an outcome. For example, each time that a patient reports that a dose has been taken, the BCPM application may request the patient to specify an outcome. If a patient is taking multiple prescriptions for multiple conditions, the BCPM application may prompt the patient to specify an outcome for each condition. For example, if the patient has arthritis and high blood pressure, the BCPM application may prompt the patient to specify their pain level for arthritis on a scale of 1-10 and to take and enter their blood pressure (or the blood pressure may be collected automatically via a Bluetooth connection from an electronic sphygmomanometer). For each reported outcome, the BCPM application may directly record in the blockchain an outcome transaction that specifies the reported outcome including date, time, condition, value, and so on. An outcome transaction may identify the dispense transaction or may directly identify the corresponding prescription transaction.

In some embodiments, the BCPM system may record in the blockchain a submission selection transaction that includes computer code for collecting and reporting on submissions by pharmacies. For example, when a prescription transaction is recorded in the blockchain, a constructor of the computer code may record a corresponding submission selection transaction. A constructor of the submission selection transaction may collect the submission information and record the submission transactions for the pharmacies. The constructor may also send to the BCPM application of the patient a notification of the submission transactions. Alternatively, the BCPM application may check the blockchain to determine whether any submission transactions have been recorded for a prescription of the patient. When the patient selects a pharmacy, the BCPM application may send a pharmacy selection message to the submission selection transaction. In response, the submission selection transaction may record in the blockchain a selected submission transaction that identifies the selected pharmacy and may notify the pharmacy of the selection.

In some embodiments, the BCPM system may create and allocate to pharmacies submission tokens for use when a pharmacy generates a submission to dispense a prescription. To allocate a submission token to a pharmacy, the BCPM system records in the blockchain a submission token transaction that creates and outputs a submission token that is owned by the pharmacy. When submission information relating to a prescription is collected from a pharmacy, the BCPM system may transfer ownership of a submission token owned by the pharmacy to the submission selection transaction or some other entity. The BCPM system may access a "wallet" or some other data store of a pharmacy to identify a submission token of the pharmacy, or a pharmacy system may provide the identification of a submission token to the BCPM system. After the patient selects a pharmacy, for each pharmacy that is not selected, the BCPM system may record in the blockchain a submission token transaction that inputs one of the submission tokens and outputs a submission token that is owned by the non-selected pharmacy. Such a submission token transaction causes ownership of a submission token to revert back to a non-selected pharmacy. The BCPM system may also record in the blockchain a submission token transaction for the selected pharmacy that inputs one of the submission tokens and outputs a submission token that is owned by a BCPM service that manages the BCPM system. The use of submission tokens can be used to limit or otherwise control submissions by pharmacies. A pharmacy may also may offer multiple submission tokens or a higher-valued submission token in exchange for a higher placement in the list of pharmacies. The BCPM service may also allocate submission tokens in exchange for some consideration.

In some embodiments, the sponsors of insurance, the manufacturers, and the pharmacies may provide incentive tokens to incentivize patients to take certain action. For example, the pharmacies may include incentive tokens as part of their submission information relating to dispensing a prescription. The submission information for a pharmacy may specify the incentive that will be provided to the patient when the patient selects the pharmacy to dispense the prescription. For example, an incentive token may specify that the patient will receive a discount when the prescription is next dispensed, a certain percentage discount for in-store or online purchases, and so on. When a pharmacy is selected, the pharmacy may record in the blockchain an incentive token transaction that creates and outputs an incentive token that is owned by the patient and defines the incentive. The BCPM application may allow a patient to review their incentive tokens and select when to redeem an incentive token. For example, if a patient wants to redeem an incentive token when making an in-store purchase, the BCPM application may display a Quick Response ("QR") code that identifies the incentive token. A point-of-sale system of a pharmacy may be augmented to interface with the BCPM system. In such a case, the point-of-sale system may scan the QR code, adjust a purchase price based on the incentive, and coordinate the recording of an incentive token transaction that inputs the incentive token that is owned by the patient and outputs an incentive token that is owned by the pharmacy. Similarly, when a patient selects an alternative medicine, the sponsor of insurance for a patient or the manufacturer may record in the blockchain an incentive token transaction that creates an incentive token that is owned by the patient that defines the incentive. For example, if the incentive is waiver of any copayment, the patient can redeem the incentive token when the prescription for the alternative medicine is dispensed. As another example, if the incentive is a manufacturer mail-in rebate, the pharmacy may print the mail-in rebate form and provide it to the patient when the alternative medicine (e.g., a branded medicine of the manufacturer) is dispensed.

In some embodiments, the BCPM system may interface with various systems to validate a prescription for a patient. The validating of a prescription may include the checking of various requirements to ensure that a pharmacy will be reimbursed by an insurer, that the prescription complies with formulary information of a sponsor, that the patient has not recently been dispensed a similar prescription, that the prescribed medicine will not interact negatively with other medicines that the patient is taking, and so on. The BCPM system may interface with existing systems and/or may be adapted to perform its own validation. The validation of a prescription may be performed when the prescription is written by a prescriber and/or when the prescription is to be dispensed. In this way, any changed circumstances between the writing and the dispensing of a prescription can be evaluated when the prescription is to be dispensed. For example, the changed circumstances may include a similar prescription written by a different prescriber being dispensed to the patient by a different pharmacy, updated drug interaction guidelines, and so on. The BCPM system may also record in the blockchain validate transactions for tracking the results of the validations.

In some embodiments, the BCPM system may employ a rules-based system for generating submissions on behalf of pharmacies. Each pharmacy may specify the rules to be used for generating its submissions. For example, one rule for a pharmacy may be that when dispensing a prescription for 30 doses of a certain medicine for a certain sponsor, the copayment amount should be $10 and the incentive should be a 25% off coupon. Another rule for the pharmacy may be that when the same conditions apply and there are refills, the copayment amount for the first refill will be $10 and for the subsequent refills will be $0. Such a rule may encourage a patient to not only obtain all their refills but also select the pharmacy as the dispensing pharmacy. Alternatively, the BCPM system may in real time interface with computer systems of the pharmacies to collect the submission information directly from the pharmacies. In such a case, a pharmacy may employ dynamic and customized techniques for optimizing their dispensing submissions in real time.

In some embodiments, the blockchain of the BCPM system may be used to perform a variety of data analytics. For example, a data analytics system may be used to recommend medicines based on outcomes reported by patients and recorded in the blockchain. The data analytics system may generate a feature vector for each patient with a certain condition and label the feature vector with the outcome. The feature vector for a patient may include demographic information, prescription information, and medical history information of the patient. The label may indicate the outcome reported by the patient. The labeled feature vectors may be used as training data to learn a model for recommending medicines, predicting outcomes, and so on. Various machine learning techniques may be used to train a model such as a support vector machine, a neural network, a convolutional neural network (e.g., with image features), a Bayesian network, a Naïve Bayesian network, learning regression, and so on. The model then can be used to recommend medicines to a patient based on the patient's demographic information, prescription information, and medical history.

In some embodiments, the BCPM system supports the maintaining of formulary information that is recorded in the blockchain. A sponsor of insurance may record in the blockchain a formulary transaction that specifies the initial formulary information and that provides code of a smart contract for accessing and maintaining the formulary information. The smart contract may process messages relating to retrieval of the formulary information by the BCPM system. For example, a message may be sent to the formulary transaction to retrieve approved alternative medicines for a prescribed medicine and/or condition. The smart contract may also process messages relating to maintaining of the formulary information. For example, a message may be sent to the formulary transaction to add an approved alternative medicine for a certain brand medicine. The BCPM system may employ machine learning techniques to automatically update or to suggest updates to the formulary information of a sponsor. For example, if the patient-reported outcomes for a medicine indicate that the medicine is not effective at treating a certain condition, then the medicine may be removed as an approved medicine for that condition. As another example, a high-cost medicine may be removed as an approved medicine when a low-cost medicine is identified by patients as being equally effective. The formulary may be implemented as conventional formulary information that is recorded in the blockchain. Alternatively, the formulary may be implemented as a classifier that is trained over time to identify approved medicines for a patient. The BCPM system may use training data such as detailed patient demographics, reported outcomes, patient adherence to prescription, and so on when applying the machine learning techniques to learn the classifier. For example, if the classifier is a neural network, the activation functions and weights that are learned may result in approved medicines and doses that can be different for different patients. As a result, the classifier can provide formulary information for each patient that is based on reported outcomes of patients that may be cohorts, even though the characteristics for being considered a cohort may not be fully understood without a detailed analysis of the training data.

FIG. 1 is a flow diagram that illustrates the overall processing of a BCPM system in some embodiments. A BCPM system 100 coordinates the overall managing of prescriptions by recording transactions in a blockchain. In block 101, the BCPM system records in the blockchain a prescription transaction that specifies details of a prescription such as the medicine, dosage, patient, and so on. In block 102, the BCPM system records in the blockchain a submission selection transaction for coordinating the selection of a pharmacy to dispense the prescription. In block 103, the BCPM system records in the blockchain a submission transaction for each pharmacy that has provided a submission for dispensing the prescription. Each pharmacy may record its own submission transaction or may send a message to the submission selection transaction so that the submission selection transaction can record the submission transaction. In block 104, the BCPM system records in the blockchain submission token transactions to transfer ownership of a submission token from a pharmacy to the submission selection transaction, the prescription transaction, or some other entity. The purpose of transferring the ownership is to ensure that the submission token has not been spent by a pharmacy and is available to be transferred to the BCPM service if that pharmacy is selected. Again, each pharmacy may record its own submission token transaction or may send a message to the submission selection transaction so that the submission selection transaction can record the submission token transaction. In block 105, the BCPM system records in the blockchain a selected submission transaction to identify the submission of a pharmacy that the patient selected to dispense the prescription. In block 106, the BCPM system records in the blockchain a submission token transaction for the selected pharmacy to transfer ownership of a submission token to the BCPM service. In block 107, the BCPM system records in the blockchain a submission token transaction for each non-selected pharmacy to transfer ownership of a submission token back to the non-selected pharmacy. In block 108, the BCPM system records in the blockchain a dispense transaction when a pharmacy dispenses the prescription to the patient. In block 109, the BCPM system records in the blockchain, for each dose of the prescription, a dose token transaction that creates and outputs a dose token with the dispense transaction as the owner. In block 110, the BCPM system records in the blockchain, for each dose of the prescription taken by the patient, a dose token transaction that inputs a dose token and outputs a dose token that is owned by the patient. The BCPM system then completes.

FIGS. 2A-2D illustrate display pages of a BCPM application in some embodiments. A display page 200 allows a patient to select an alternative to a prescribed medicine. The display page includes a prescription information area 201 and an alternative medicine area 202. The prescription information area displays information on the prescription such as medicine, dose, refills, and so on. The alternative medicine area displays information on each alternative to the prescribed medicine. The alternative medicine area displays, for each alternative medicine, a sub-area that identifies an alternative medicine, a copayment amount, an incentive, and a patient total cost. A user may select a sub-area to indicate selection of an alternative medicine. In response to the selection of an alternative medicine, the BCPM system records a selected alternative medicine transaction and, if an incentive is offered, a transaction to create an incentive token that is owned by the patient. The BCPM application may also detect that a patient is in the prescriber's office (e.g., based on Global Positioning System information or a selection by the patient) and provide a user interface that allows a more interactive experience with the prescriber. For example, the BCPM application may provide a user interface that guides the patient through recommended questions to help in evaluating in consultation with the prescriber the cost/benefit tradeoffs of the different medicines, different dosages, different delivery mechanisms, and so on. The BCPM application may also notify the prescriber system that the patient is in the prescriber's office so that information provided to the patient may also be provided to the prescriber.

A display page 210 allows a patient to select a pharmacy to dispense a prescription. The display page includes a prescription information area 211 and a pharmacy submission area 212. The prescription information area displays information on the prescription such as medicine, dose, refills, and so on. The pharmacy submission area displays information on each submission by a pharmacy to dispense the prescription. The pharmacy submission area displays, for each submission, a sub-area that identifies a pharmacy, a copayment amount, and an incentive. A user may select a sub-area to indicate selection of a pharmacy to dispense the prescription. In response to the selection of a pharmacy, the BCPM system records a selected submission transaction and submission token transactions to transfer ownership of the submission tokens. In some embodiments, the BCPM application may also include a user interface to allow a patient to transfer a prescription to a different pharmacy. When a patient selects a transfer prescription option, the BCPM system may repeat the submission selection process resulting in the recording of new selected submission transaction indicating the pharmacy to which the prescription is to be transferred.

A display page 220 allows a patient to report that a dose of a prescription has been taken. The display page includes a prescription selection area 221, a quantity selection area 222, a time taken area 223, and a submit button 224. The prescription selection area includes a drop-down list of the prescriptions that have been dispensed but whose doses have not been completely taken. The patient selects the prescription from the drop-down list. The quantity selection area includes a drop-down list for as selecting the quantity of the medicine has been taken. For example, a patient may be instructed to take one to three pills at a time as needed. The patient selects the quantity from the drop-down list. The time taken area, which may be pre-populated with the current time, allows the user to enter the time at which the dose was taken. After entering the dose information, the patient selects the submit button. In response to selecting the submit button, the BCPM system may record in the blockchain a dose token transaction to transfer ownership of a dose token for the dispensed prescription to the patient.

A display page 230 allows a patient to report an outcome for a prescription. The display page includes a condition selection area 231, an outcome selection area 232, a time reporting area 233, and a submit button 234. The condition selection area includes a drop-down list of the conditions (e.g., arthritis) for which prescriptions have been written. The patient selects from the drop-down list the condition whose outcome is to be reported. The outcome selection area includes a drop-down list of the possible outcomes for the selected condition. For example, the possible outcomes may be a pain level of 0-10, for example, using the Wong-Baker Faces Pain Rating Scale. The patient selects from the drop-down list the outcome that is to be reported. The time reporting area, which may be pre-populated with the current time, allows the user to enter the time at which the outcome was determined. In response to selecting the submit button, the BCPM system may record in the blockchain an outcome transaction to report the outcome for the patient.

In some embodiments, the BCPM application may also provide a user interface for accessing online drug consultation information. The drug consultation information may include general usage information provided by the manufacturer or a health organization (e.g., National Institute of Health or the Mayo Clinic), patient-specific usage information provides the patient's prescriber or pharmacist, side-effect information, and so on. The BCPM application may integrate a communications mechanism that allows a patient to exchange messages with a care provider. For example, the BCPM application may interface with existing patient portals that support such messaging and provide online access to patient records.

In some embodiments, the BCPM application may be hosted on a cloud system that interfaces with a variety of client devices. For example, the client devices may include Internet-of-Thing devices such as a fitness tracking device (e.g., worn on the wrist), a personal digital assistant, an intelligent personal assistant (e.g., Alexa by Amazon), a smart device, and so on. These client devices may support a voice interface to receive commands and information, output of information using audio and/or a screen, and so on. The BCPM application accesses the blockchain and receives and sends information via the Internet, a cellular network, a satellite network, and so on. The BCPM application may also include interfaces to retrieve health information from various applications that of the client devices. For example, if a client device is capable of taking measurements such as blood pressure, heart rate, body temperature, activity level (e.g., number of steps), weight, and so on, the BCPM system can retrieve these measurements as the heath information and record them in the blockchain. The health information may also include information entered by the patient such as ratings of pain level, area of discomfort (e.g., head or lower back), non-prescription medicines and vitamins, diet information, sleep patterns, and so on. The health information can be used to help evaluate the overall effectiveness of a medicine. The BCPM system may provide incentive tokens to a patient when their client device is registered to use the BCPM application and when the patient permits the BCPM application to access the patient's health information.

In some embodiments, the BCPM system may provide various notifications and alerts to a patient. For example, the BCPM system may notify a patient when a new prescription for the patient has been recorded in the blockchain, when the patient is to take a dose (e.g., in the morning and the evening), when to order a refill, when the patient is to take some action previously specified by the patient or the prescriber (e.g., schedule an appointment or report an outcome), and so on. When notifying the patient to take a dose, the BCPM application may request that the patient confirm that a dose for the correct prescription is being taken. For example, the container for the medicine may include a QR code that can be scanned by the BCPM application, may be enabled to send a message electronically (e.g., via a near-field communication) to the BCPM application when the container is opened, and so on. The BCPM system may also alert a patient of certain conditions identified from the health information such as high blood pressure, low heart rate, expected versus reported outcomes, and so on. The BCPM system may maintain a log of these notifications and alerts. In addition, the BCPM system may allow a patient to set reminders, for example, to discuss a medical issue with the physician during the next visit. The BCPM application may detect when the patient is a physician's office and provide the reminders to the patient or directly to the physician as topics for discussion.

Figure 3:
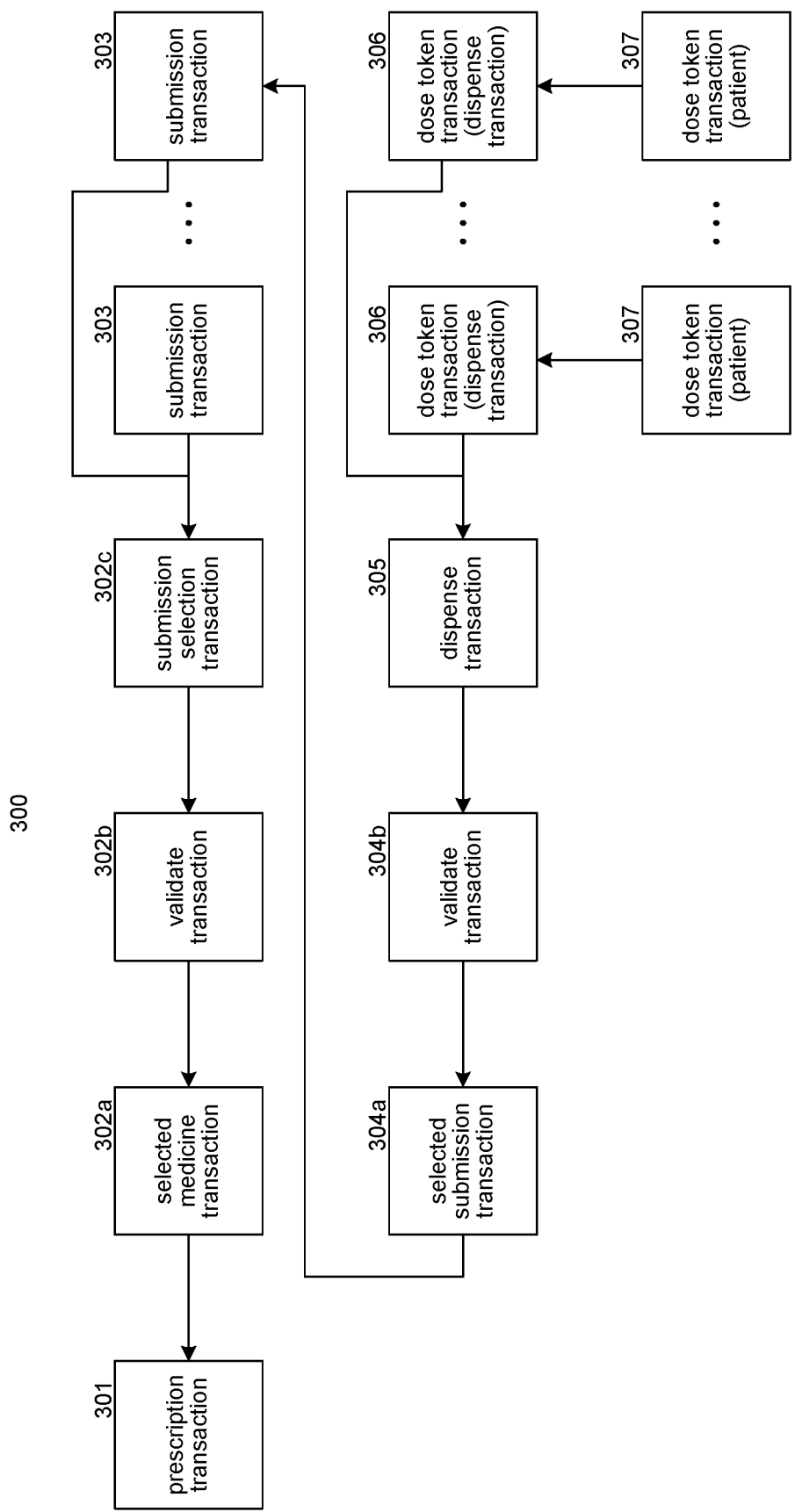
FIG. 3 is a block diagram that illustrates a blockchain of the BCPM system in some embodiments.

FIG. 3 is a block diagram that illustrates a blockchain of the BCPM system in some embodiments. A blockchain 300 illustrates some transactions that have been recorded by the BCPM system. A prescription transaction 301 may be recorded when a prescriber writes a prescription and may include information describing the prescription or may include a reference to a database entry describing the prescription along with a hash of the database entry. A submission selection transaction 302c, which may be recorded when a constructor of the prescription transaction executes, may reference the prescription transaction. A constructor of the submission selection transaction may coordinate the soliciting of submissions from pharmacies and recording of submission transactions corresponding to submissions by pharmacies. Submission transactions 303 may reference the submission selection transaction and describe the submission by a pharmacy. A selected submission transaction 304a, which may be recorded when a patient selects a pharmacy, may reference the submission transaction of the selected pharmacy, the submission selection transaction, and/or the prescription transaction. A validate transaction 304b may be recorded after the BCPM system determines whether the prescription with the selected medicine is valid to be dispensed by the selected pharmacy. A dispense transaction 305, which may be recorded when a pharmacy dispenses the prescription, may reference the selected submission transaction and include details related to the dispensing of this prescription, such as the date of the dispensing of the prescription, a medicine that was substituted in place of the prescribed medicine, and so on. Dose token transactions 306, which may be recorded when a prescription is dispensed, create dose tokens that may be owned by the dispense transaction. Dose token transactions 307, which may be recorded when a patient takes a dose of the prescription, transfer ownership of a dose token to the patient.

Figure 4:
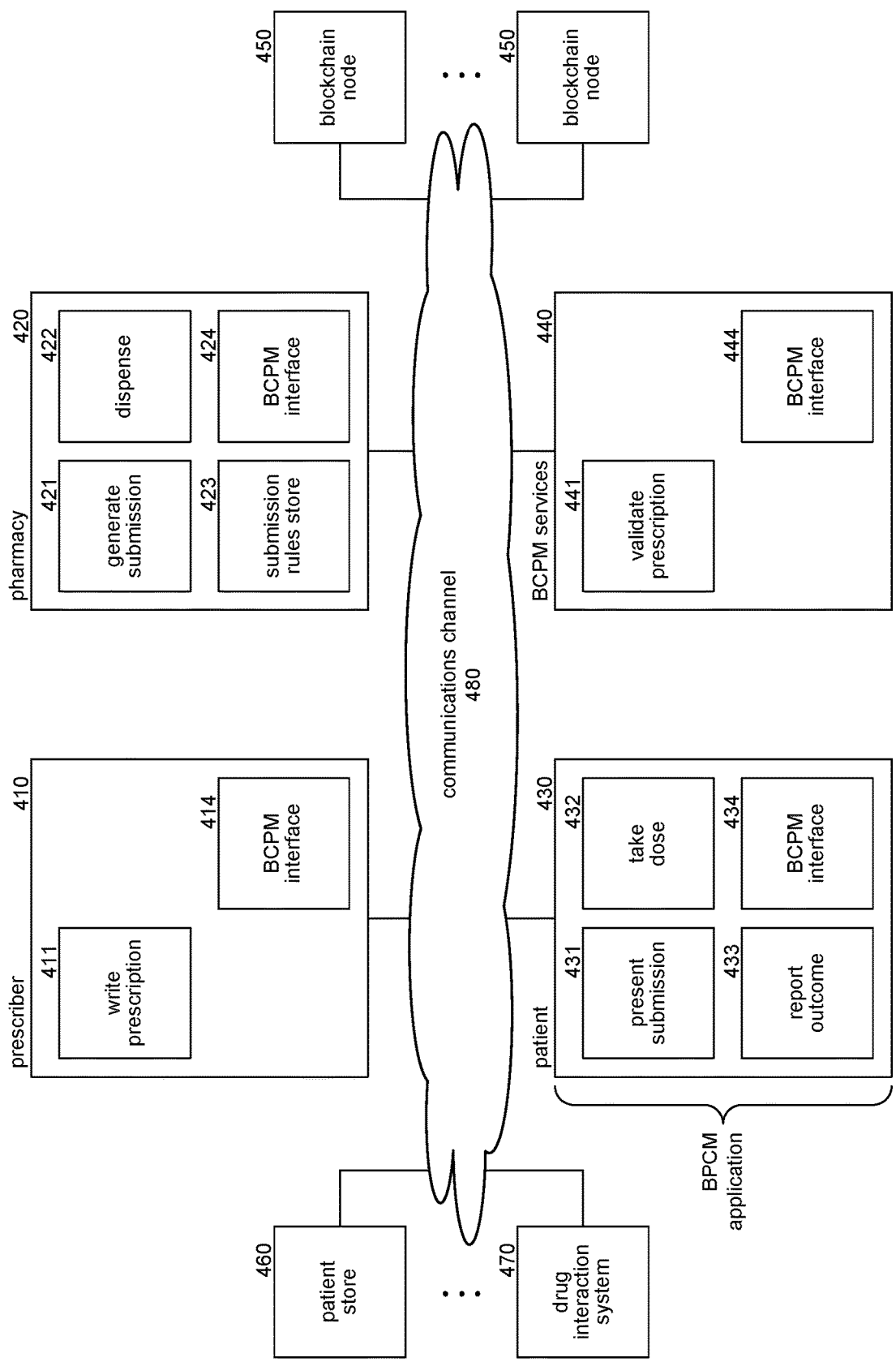
FIG. 4 is a block diagram that illustrates systems that implement the BCPM system in some embodiments.

FIG. 4 is a block diagram that illustrates systems that implement the BCPM system in some embodiments. The BCPM system may be implemented by or interface with a prescriber system 410, a pharmacy system 420, a patient system 430, a BCPM service 440, blockchain nodes 450, a patient store 460, and a drug interaction system 470, all of which may communicate via communications channel 480.

A prescriber system may be an existing prescriber system that includes a write prescription component 411 augmented with a BCPM interface 414. The write prescription component allows a prescriber to write a prescription that is recorded in the blockchain. The BCPM interface interfaces with the blockchain nodes to access the blockchain to retrieve transactions, record transactions, send messages to transactions, and so on.

The pharmacy system may include a generate submission component 421, a dispense submission component 422, a submission rules store 423, and a BCPM interface 424. The generate submission component coordinates the generating of submissions by a pharmacy to dispense a prescription, for example, by applying rules for each pharmacy stored in the submission rules store. The dispense component coordinates the dispensing of a prescription to a patient. The generate submission component and the dispense component may invoke the BCPM interface to record in the blockchain submission transactions, submission token transactions, dispense transactions, dose token transactions, and so on. The pharmacy system may also include a component to record a prescription in the blockchain. For example, a prescriber who is not using the BCPM system may write prescription on paper that the patient takes to a pharmacy. The pharmacy that is using the BCPM system can record the prescription in the blockchain. The pharmacy system may also record a submission selection transaction to indicate that it was selected as the pharmacy. The BCPM system may also support the recording of a submission selection transaction and corresponding submission transactions. If the patient has access to the BCPM application, the patient may decide to select a different pharmacy to dispense the prescription. The pharmacy system may also support receiving payment, for example, for medicines not covered by insurance or if prescription has not yet been approved by the insurer. The payment may be paid in fiat currency or a cryptocurrency (e.g. Bitcoin). In either case, the pharmacy system may interface with an exchange to determine current exchange rate and to exchange the payment into a different currency. The pharmacy system may also allow a pharmacy to record in the blockchain transactions relating to refills, renewals, changes, and so on relating to a prescription.

A patient system, which may be a device with a BCPM application, may include a present submission component 431, a take dose component 432, a report outcome component 433, and a BCPM interface 434. The present submission component may access the blockchain via the BCPM interface to retrieve the submission transactions of pharmacies, display information on the submissions, receive the selection of a pharmacy, and record a selected submission transaction or send a selected submission message to a submission selection transaction. The take dose component may display information relating to prescriptions, receive indications of a dose that has been taken for a selected prescription, and record a dose token transaction to transfer ownership of a dose token to the patient or send a dose token message to a dispense transaction, which then records the dose token transaction. The report outcome component may display information on conditions of a patient, receive an outcome for a selected condition, and record an outcome transaction. The components of the patient system invoke the BCPM interface to access the blockchain.

The BCPM service may include a validate prescription component 441 and a BCPM interface component 444. The validate prescription component is invoked to determine whether a prescription is valid for the patient based on, for example, drug interactions and similar prescriptions. Each blockchain node may maintain a separate copy of the blockchain. The blockchain nodes may communicate with each other to ensure that blocks are properly created, mined, and stored. Alternatively, the BCPM system may record the transactions in a distributed ledger that is not a blockchain, such as the Corda system. The patient store may include databases that store the medical history, demographic information, and so on of patients. The drug interaction system may provide an application programming interface for accessing information describing negative interactions between various drugs. The communications channel allows the various systems to send communications and may be implemented using mechanisms such as the Internet, a cellular system, a satellite system, and so on. Aspects of the BCPM system may be implemented with smart contracts for various transactions (e.g., non-token transactions), with code that executes on the computer systems, and so on.

Although not illustrated in FIG. 4, the systems that implement the BCPM system may also include a formulary service, a pricing service, and a notification service. The formulary service may support the accessing and maintaining of formulary information for a sponsor and may implement machine learning techniques to update the formulary or learn a formulary classifier. The formulary classifier may input a feature vector for a patient that is derived from patient demographics, condition of the patient, patient health records, and so on and outputs a formulary that is customized to that patient. The pricing service may allow sponsors and pharmacies to interact to establish a price at which a pharmacy is to provide a medicine to patients of the sponsors. For example, the pricing service may allow a sponsor to elicit pricing proposals from the pharmacies and to send counterproposals. The proposals and counterproposals may specify prices, volume discounts, incentives, and so on. Once an agreement is reached, the pricing service may support the generating of rules (to be approved by the parties) that implement the agreement. The parties may record a price transaction that specifies the rules and provides a smart contract. When the price transaction receives a submission message, the smart contract applies the rules to generating the price and incentive per the agreement. The notification service may maintain a database of contact information for participants (e.g., prescribers, pharmacies, and patients) in the BCPM system such as telephone numbers, electronic mail addresses, BCPM identifiers, and so on. The database may also include permission information to specify the type of notifications (if any) that are allowed between the participants. Upon receiving a request to send a notification to a participant, the notification service logs the request, checks the permissions, and sends the notification to a device (e.g., via text message or electronic mail message) to the participant.

The computing systems (e.g., network nodes or collections of network nodes) on which the BCPM system may be implemented may include a central processing unit, input devices, output devices (e.g., display devices and speakers), storage devices (e.g., memory and disk drives), network interfaces, graphics processing units, cellular radio link interfaces, global positioning system devices, and so on. The input devices may include keyboards, pointing devices, touch screens, gesture recognition devices (e.g., for air gestures), head and eye tracking devices, microphones for voice recognition, and so on. The computing systems may include desktop computers, laptops, tablets, e-readers, personal digital assistants, smartphones, gaming devices, servers, and so on. The computing systems may access computer-readable media that include computer-readable storage media and data transmission media. The computer-readable storage media are tangible storage means that do not include a transitory, propagating signal. Examples of computer-readable storage media include memory such as primary memory, cache memory, and secondary memory (e.g., DVD) and other storage. The computer-readable storage media may have recorded on them or may be encoded with computer-executable instructions or logic that implements the BCPM system. The data transmission media are used for transmitting data via transitory, propagating signals or carrier waves (e.g., electromagnetism) via a wired or wireless connection. The computing systems may include a secure cryptoprocessor as part of a central processing unit for generating and securely storing keys and for encrypting and decrypting data using the keys.

The BCPM system may be described in the general context of computer-executable instructions, such as program modules and components, executed by one or more computers, processors, or other devices. Generally, program modules or components include routines, programs, objects, data structures, and so on that perform tasks or implement data types of the BCPM system. Typically, the functionality of the program modules may be combined or distributed as desired in various examples. Aspects of the BCPM system may be implemented in hardware using, for example, an application-specific integrated circuit ("ASIC") or field programmable gate array ("FPGA").

Figure 5:
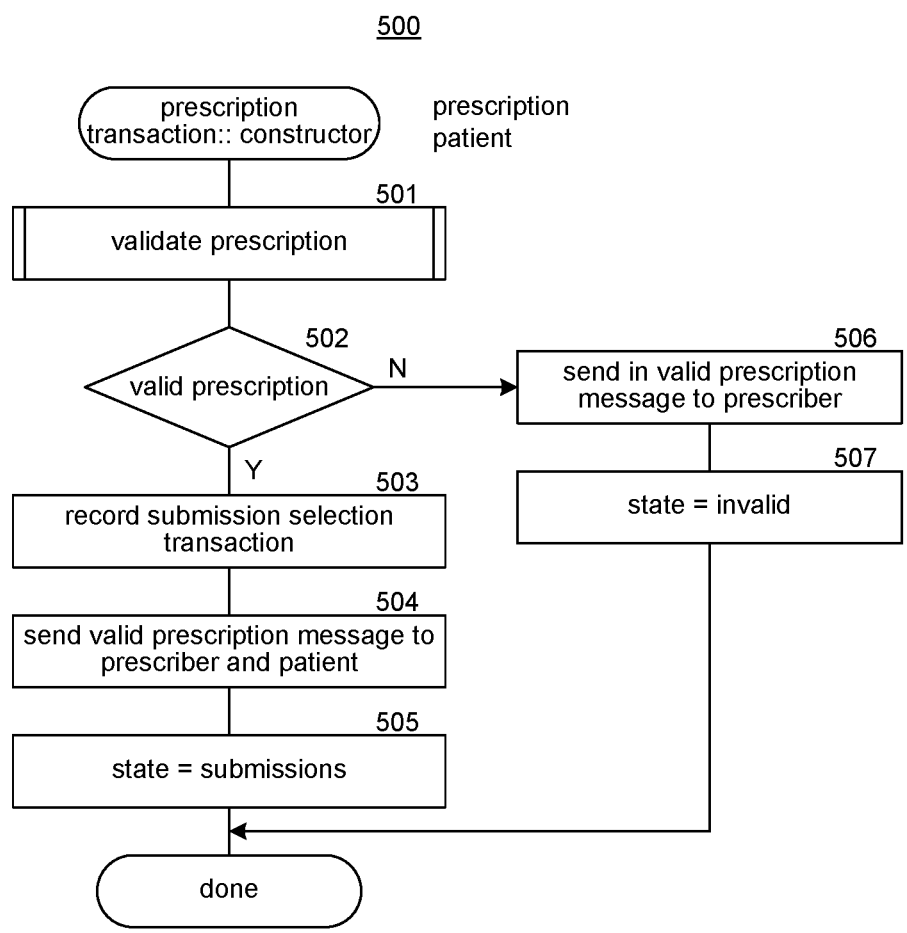
FIG. 5 is a flow diagram that illustrates the processing of a constructor of a prescription transaction in some embodiments.

FIG. 5 is a flow diagram that illustrates the processing of a constructor of a prescription transaction in some embodiments. A constructor component 500 may be invoked when a prescription transaction is instantiated when recorded in the blockchain. The component may be passed an indication of a prescription and a patient. In block 501, the component invokes a validate prescription component to determine whether the prescription is valid for the patient. In decision block 502, if the prescription is valid, then the component continues at block 503, else the component continues at block 506. In block 503, the component records in the blockchain a submission selection transaction to coordinate the receiving of submissions from pharmacies and the selection of a pharmacy. In block 504, the component sends a valid prescription message to the prescriber system and the patient system to inform these systems that the prescription can be written. In block 505, the component sets the state of the prescription transaction to "submissions" to indicate that the submissions are being coordinated and then completes. The state may be used to quickly identify the status of a prescription. The states may include submissions, waiting to be dispensed, dispensed, invalid, and so on. In block 506, the component sends an invalid prescription message to the prescriber system. In block 507, the component sets the state of the prescription transaction to "invalid" and then completes.

Figure 6:
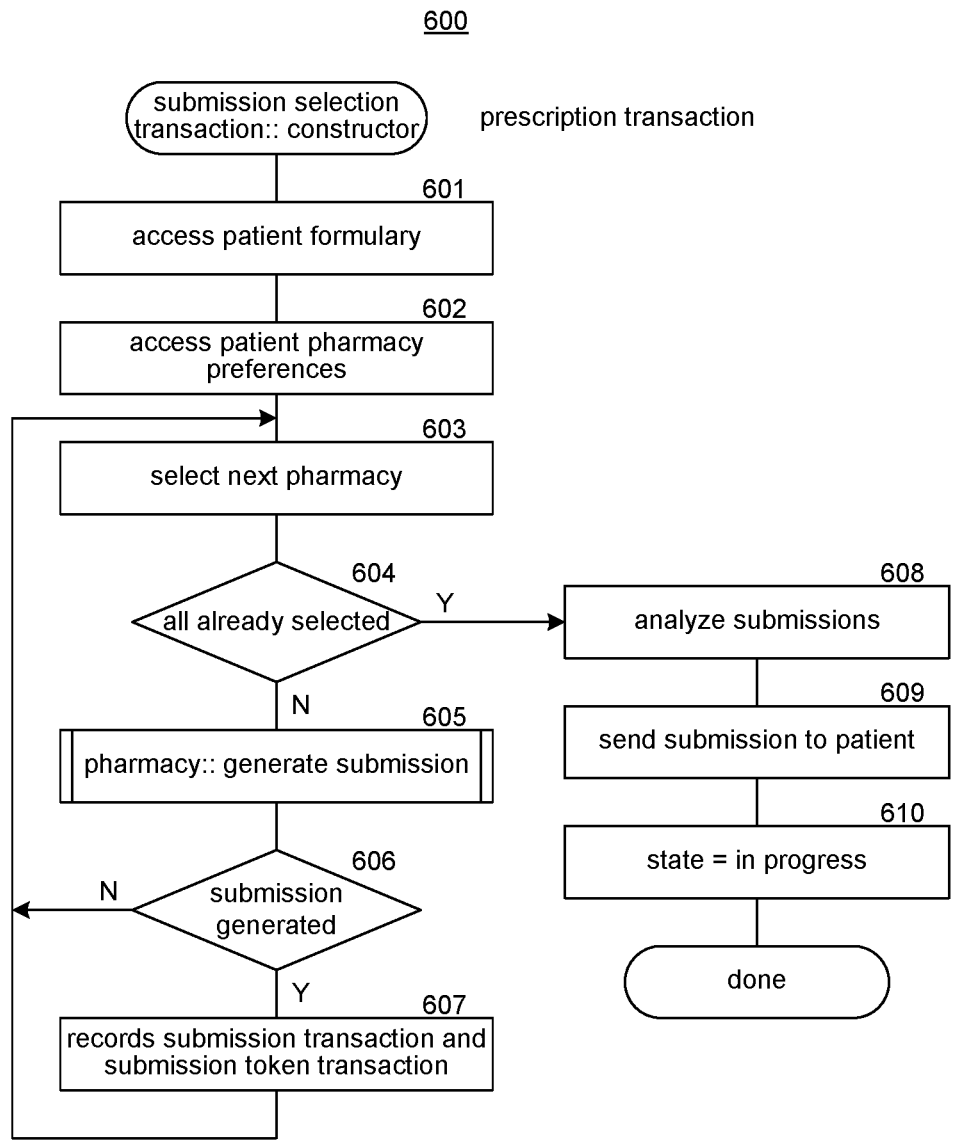
FIG. 6 is a flow diagram that illustrates the processing of a constructor of a submission selection transaction in some embodiments.

FIG. 6 is a flow diagram that illustrates the processing of a constructor of a submission selection transaction in some embodiments. A constructor component 600 may be invoked when a submission selection transaction is instantiated. The component is passed a reference to the prescription transaction. In block 601, the component accesses formulary information for the patient. The formulary information may be stored in the patient store. In block 602, the component may access patient pharmacy preference information on preferred pharmacies, prior dispensing pharmacies, approved pharmacies, and so on. In block 603, the component selects a next pharmacy. In decision block 604, if all the pharmacies have already been selected, then the component continues at block 608, else the component continues at block 605. In block 605, the component invokes a generate submission component of the pharmacy system to generate a submission for filling the prescription of the prescription transaction. In decision block 606, if a submission was generated, then the component continues at block 607, else the component loops to block 603 to select the next pharmacy. In block 607, the component records a submission transaction and a submission token transaction for the selected pharmacy. The submission token transaction transfers ownership of the submission token from the pharmacy to the submission selection transaction or some other entity. The component then loops to block 603 to select the next pharmacy. In block 608, the component analyzes the submissions to determine those that are appropriate to present to the patient. The component may select those submissions that are deemed to be most favorable to the patient based on some favorability criterion such as price, incentive, and so on. Also, the component may order the submissions based on favorability, which also may help if the BCPM application is executing on a device of a patient with a small screen (e.g., a smartphone). In block 609, the component sends the submissions to the patient system. In block 610, the component sets the state of the submission selection transaction to "in progress" and then completes.

Figure 7:
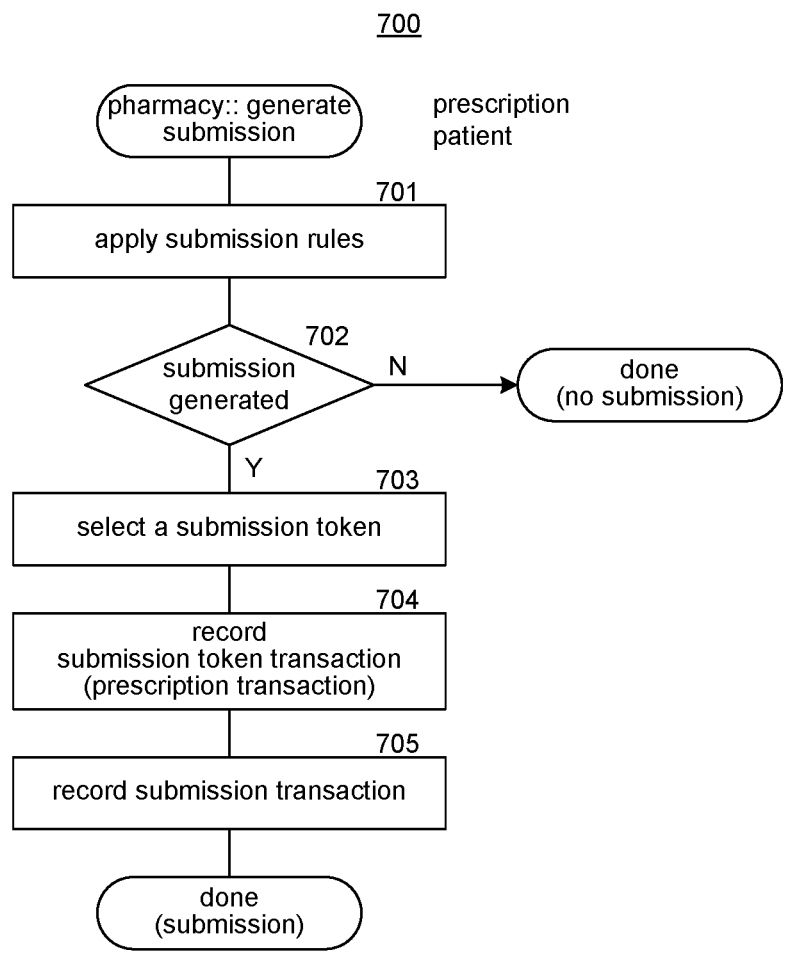
FIG. 7 is a flow diagram that illustrates the processing of a generate submission component of a pharmacy system in some embodiments.

FIG. 7 is a flow diagram that illustrates the processing of a generate submission component of a pharmacy system in some embodiments. A generate submission component 700 is passed an indication of a prescription and a patient and determines whether the pharmacy should generate a submission for dispensing the prescription. In block 701, the component may apply rules for the pharmacy to determine whether to generate a submission and, if so, the details of the submission. In decision block 702, if a submission is generated, then the component continues at block 703, else the component completes with an indication that no submission was generated. In block 703, the component selects a submission token currently owned by the pharmacy, for example, from a wallet of the pharmacy. In block 704, the component records a submission token transaction to transfer ownership of the submission token to the submission selection transaction, the description transaction, or other entity. In block 705, the component records a submission transaction for the pharmacy. The component then completes, indicating that a submission was generated.

Figure 8:
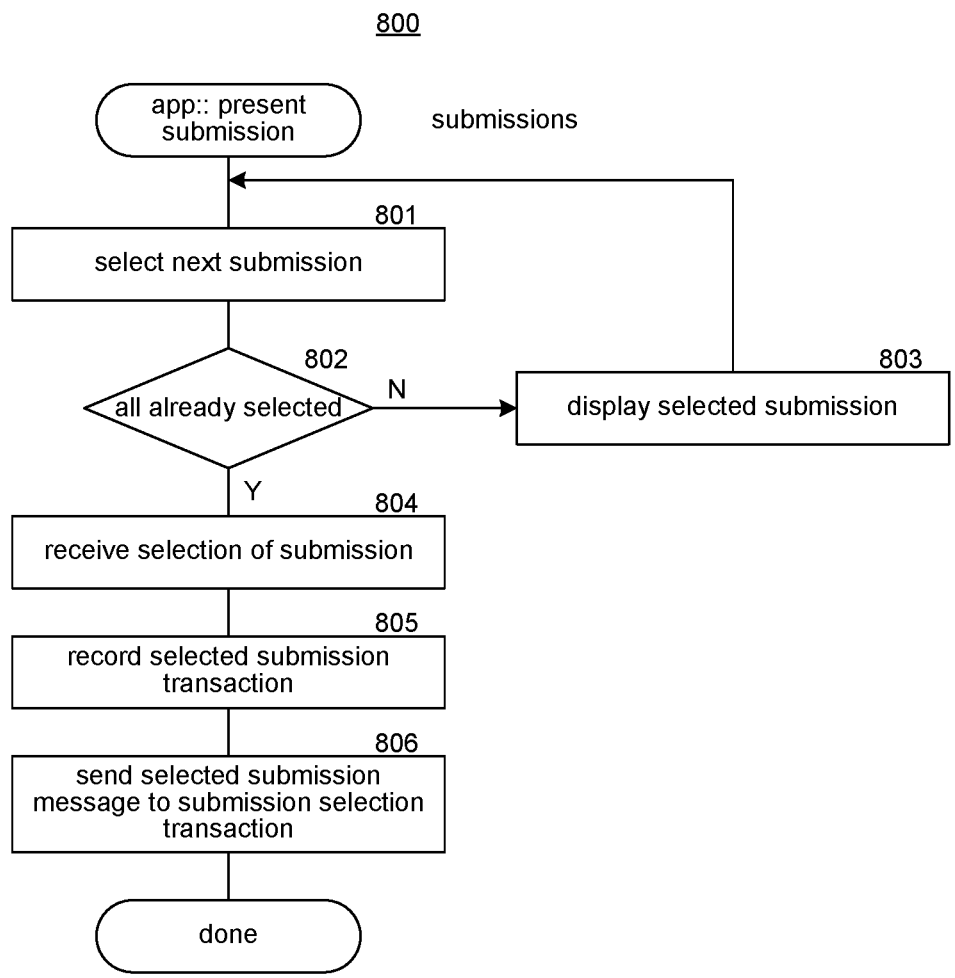
FIG. 8 is a flow diagram that illustrates the processing of a present submission component of an application of a patient system in some embodiments.

FIG. 8 is a flow diagram that illustrates the processing of a present submission component of an application of a patient system in some embodiments. A present submission component 800 is invoked passing submissions that are to be presented to a patient. In block 801, the component selects the next submission, which may be ordered based on favorability. In decision block 802, if all the submissions have already been selected, then the component continues at block 804, else the component continues at block 803. In block 803, the component displays the selected submission and then loops to block 801 to select the next submission. In block 804, the component receives a selection of a displayed submission. In block 805, the component records a selected submission transaction. In block 806, the component sends a submission selection message to the submission selection transaction and then completes.

Figure 9:
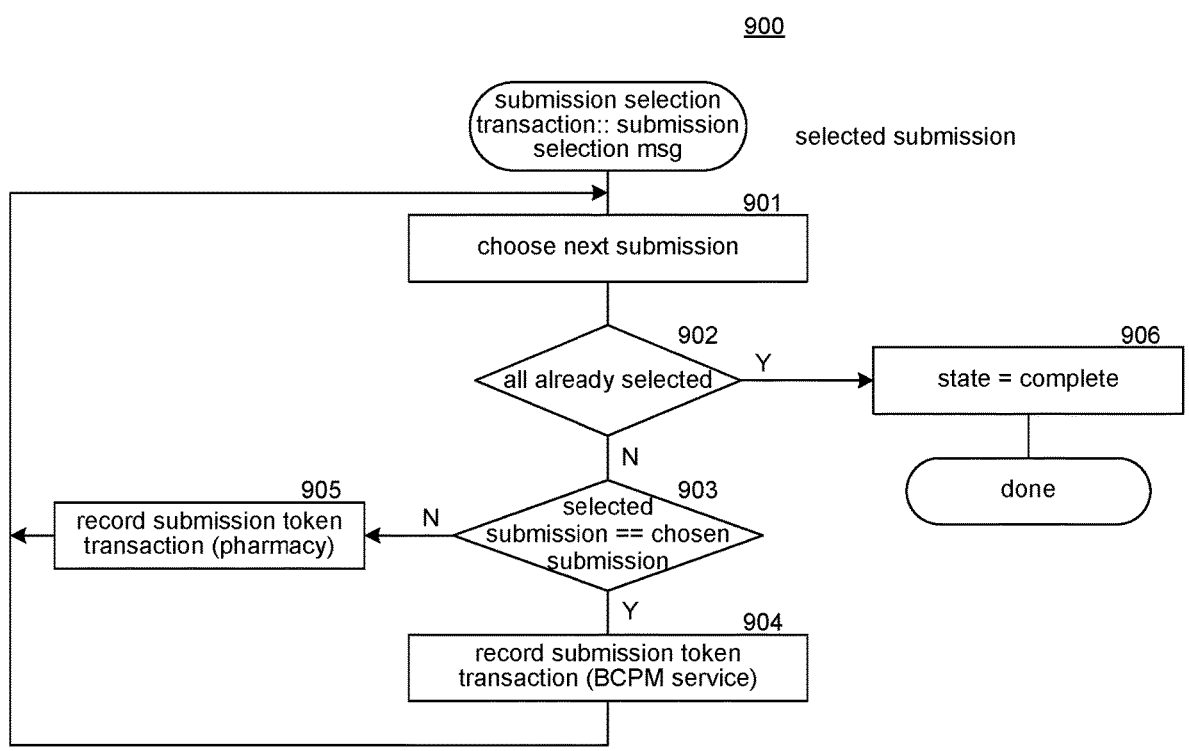
FIG. 9 is a flow diagram that illustrates the processing of a submission selection message component of a submission selection transaction in some embodiments.

FIG. 9 is a flow diagram that illustrates the processing of a submission selection message component of a submission selection transaction in some embodiments. A submission selection message component 900 is invoked when a submission selection transaction receives a submission selection message. In block 901, the component chooses the next submission, which is recorded in the blockchain as a submission transaction. In decision block 902, if all the submissions have already been selected, then the component continues at block 906, else the component continues at block 903. In decision block 903, if the selected submission indicated by the message is the chosen submission, then the component continues at block 904, else the component continues at block 905. In block 904, the component records a submission token transaction indicating that the BCPM service is the owner of a submission token and then loops to block 901 to choose the next submission. In block 905, the component records a submission token transaction that transfers ownership of a submission token to the chosen pharmacy and then loops to block 901 to choose the next submission. In block 906, the component sets the state of the submission selection transaction to "complete" and then completes.

Figure 10:
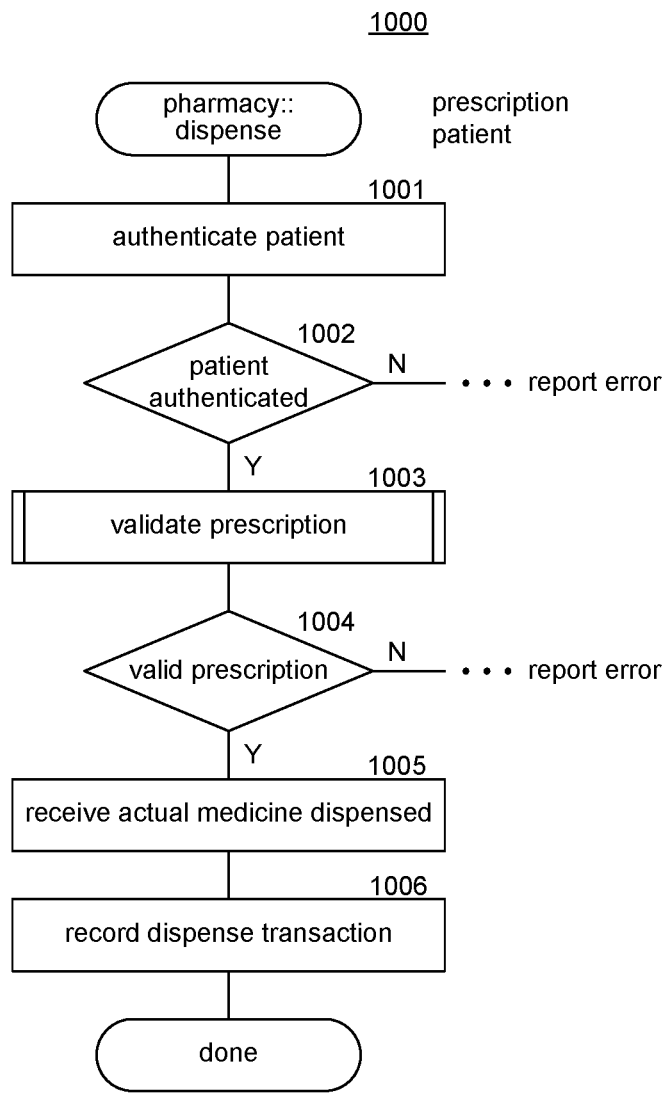
FIG. 10 is a flow diagram that illustrates the processing of a dispense component of a pharmacy system in some embodiments.

FIG. 10 is a flow diagram that illustrates the processing of a dispense component of a pharmacy system in some embodiments. A dispense component 1000 is invoked when a pharmacy dispenses a prescription. In block 1001, the component may coordinate the authentication of the patient, for example, using a fingerprint scan, checking an identification of the patient, and so on. In decision block 1002, if the patient is authenticated, then the component continues at block 1003, else the component reports an error. In block 1003, the component invokes a validate prescription component to check whether the prescription is still valid. In decision block 1004, if the prescription is valid, then the component continues at block 1005, else the component reports an error. In block 1005, the component receives an indication of the actual medicine that was dispensed, given that the pharmacy may have dispensed a substitute medicine per terms of the formulary. In block 1006, the component records a dispense transaction and then completes.

Figure 11:
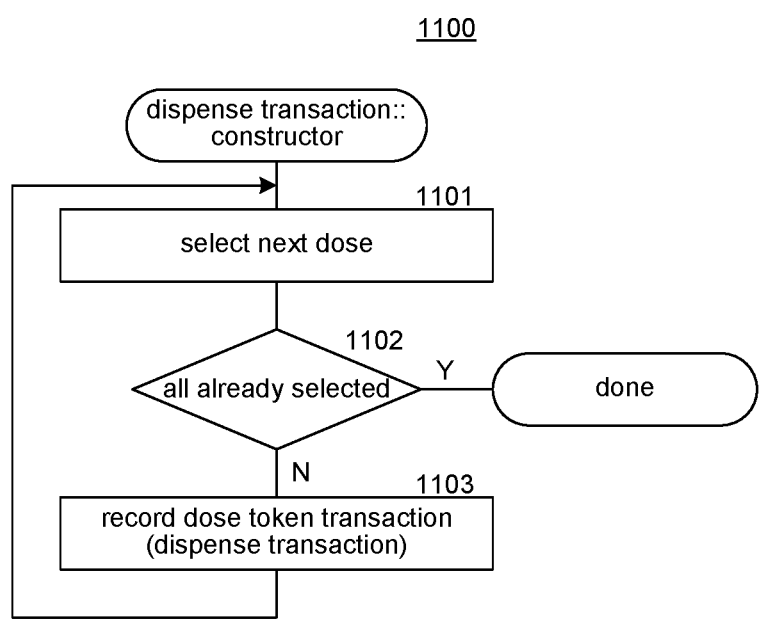
FIG. 11 is a flow diagram that illustrated the processing of a constructor of a dispense transaction in some embodiments.

FIG. 11 is a flow diagram that illustrated the processing of a constructor of a dispense transaction in some embodiments. A constructor 1100 is invoked when a dispense transaction is instantiated. In block 1101, the component selects the next dose for the prescription to be dispensed. In decision block 1102, if all the doses have already been selected, then the component completes, else the component continues at block 1103. In block 1103, the component records a dose transaction that is owned by the dispense transaction and then loops to block 1101 to select the next dose.

Figure 12:
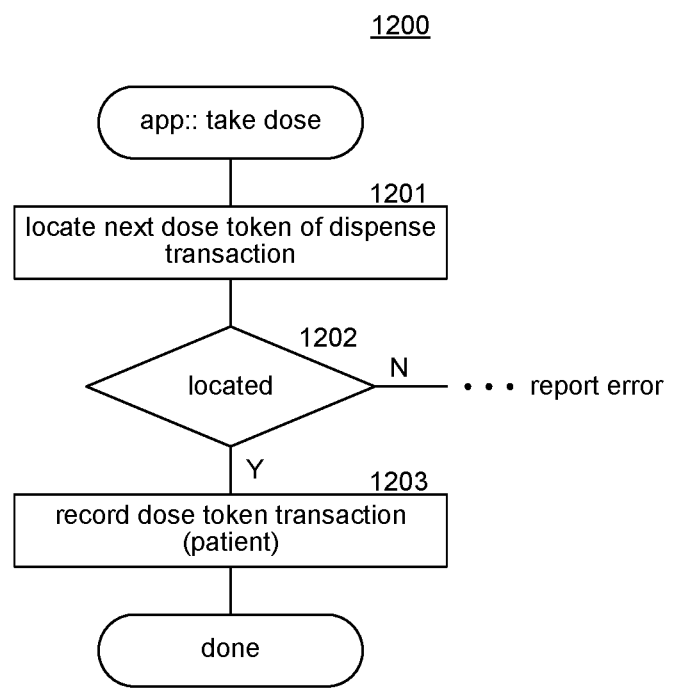
FIG. 12 is a flow diagram that illustrates the processing of a take dose component of an application of a patient system in some embodiments.

FIG. 12 is a flow diagram that illustrates the processing of a take dose component of an application of a patient system in some embodiments. A take dose component 1200 is invoked to record that the patient has taken a dose of a prescription. In block 1201, the component locates in the blockchain a next dose token of the dispense transaction. In decision block 1202, if a dose token has been located, then the component continues at block 1203, else the component reports an error. In block 1203, the component records a dose transaction to transfer ownership of the dose token to the patient. The component then completes. The BCPM system may provide incentive tokens to a patient when a dose is taken to incentivize the patient to take doses as prescribed.

Figure 13:
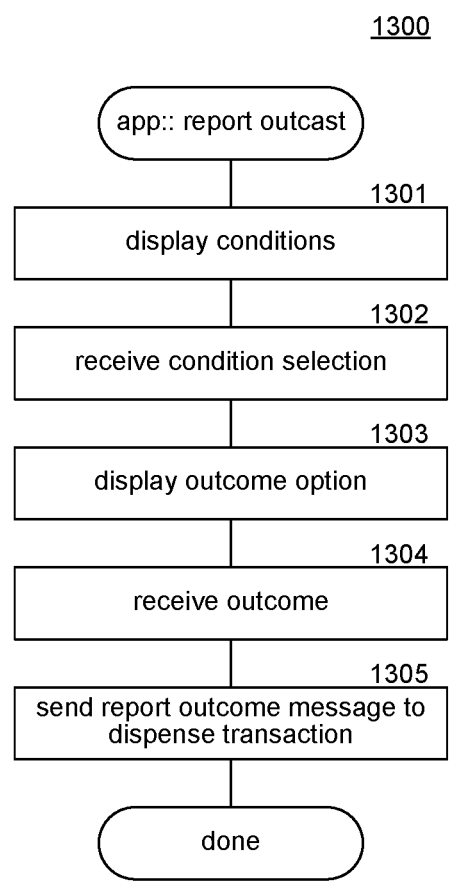
FIG. 13 is a flow diagram that illustrates the processing of a report outcome component of an application of the patient system in some embodiments.

FIG. 13 is a flow diagram that illustrates the processing of a report outcome component of an application of the patient system in some embodiments. A report outcome component 1300 is invoked to process a patient-reported outcome. In block 1301, the component displays the conditions for which the patient is being treated by various prescriptions. In block 1302, the component receives a selection of a condition for which the patient wants to report an outcome. In block 1303, the component displays outcome options for the selected condition. In block 1304, the component receives the selection of an outcome from the patient. In block 1305, the component sends the report outcome message to the dispense transaction and then completes. When the dispense transaction receives a report outcome message, the dispense transaction may record the corresponding outcome transaction. Alternatively, the application records the outcome transaction. The BCPM system may provide incentive tokens to a patient when a patient reports an outcome to incentivize the patient to report outcomes.

Figure 14:
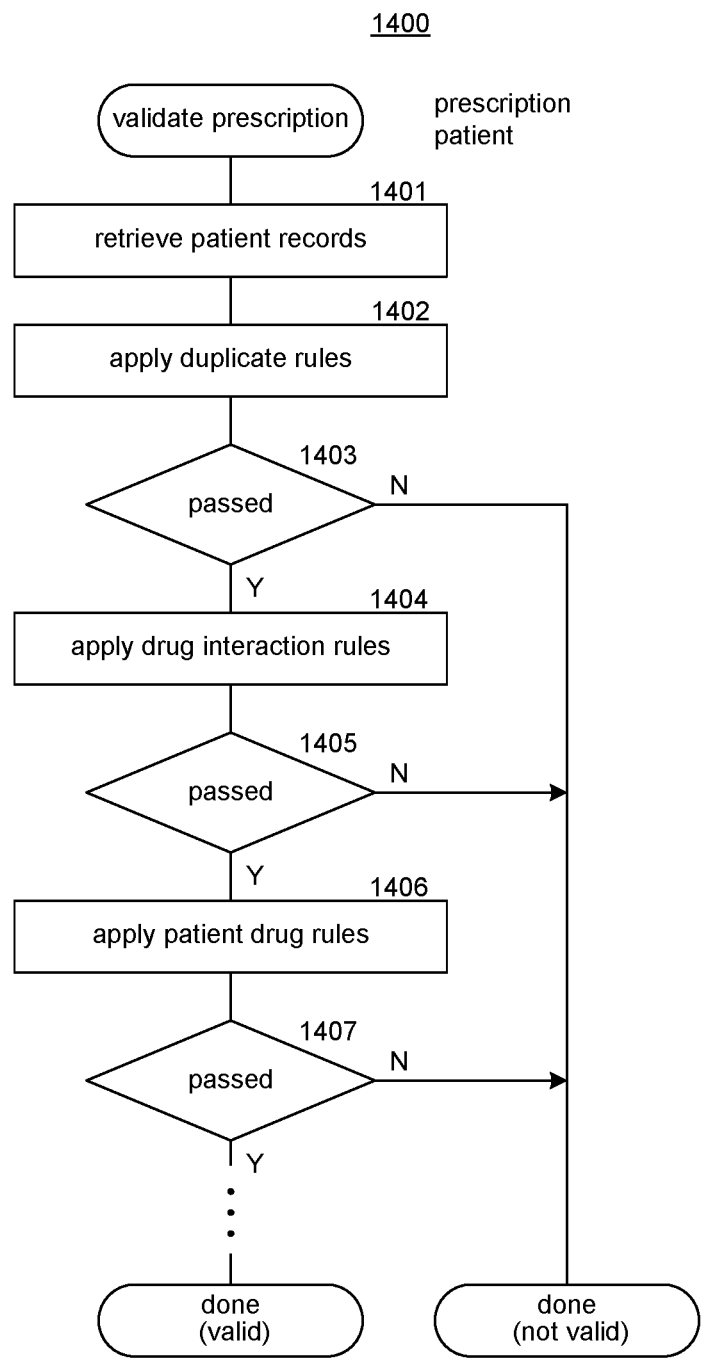
FIG. 14 is a flow diagram that illustrates the processing of a validate prescription component in some embodiments.

FIG. 14 is a flow diagram that illustrates the processing of a validate prescription component in some embodiments. A validate prescription component 1400 is passed an indication of a prescription and a patient and determines whether the prescription is valid for the patient. In block 1401, the component retrieves records for the patient from the patient store. In block 1402, the component applies duplicate rules to determine whether the prescription is a duplicate or near duplicate prescription for the patient. For example, a prescriber may have provided the same prescription twice, different prescribers may have prescribed similar prescriptions within a short time period, a prescription that seem to fraudulent, and so on. In decision block 1403, if the duplicate rules are passed, then the component continues at block 1404, else the component completes with an indication that the prescription is not valid. In block 1404, the component applies drug interaction rules to the prescription and patient. In decision block 1405, if the drug interaction rules are passed, then the component continues at block 1406, else the component completes with an indication that the prescription is not valid. In block 1406, the component applies patient drug rules to determine whether the prescription is appropriate for the patient. In decision block 1407, if the patient drug rules are passed, then the component may apply other types of rules and, if these rules are passed, the component completes with an indication that the prescription is valid, else the component completes with an indication that the prescription is not valid.

The following paragraphs describe various embodiments of aspects of the BCPM system. An implementation of the BCPM system may employ any combination of the embodiments. The processing described below may be performed by a computing device with a processor that executes computer-executable instructions stored on a computer-readable storage medium that implements the BCPM system.

In some embodiments, a method performed by one or more computing systems for selecting a pharmacy for dispensing a prescription is provided. The method receives an indication of a prescription transaction for a patient. The prescription transaction is recorded in a distributed ledger. For each of a plurality of pharmacies, the method receives a submission for dispensing the prescription. The method receives an indication that the patient has selected a pharmacy to dispense the prescription based on the submissions. The method records in the distributed ledger an indication of the dispensing pharmacy. In some embodiments, the prescription transaction includes a smart contract that records in the distributed ledger a submission selection transaction with a smart contract that controls the selecting of the pharmacy for dispensing the prescription. In some embodiments, for each submission of a pharmacy, a submission token transaction is recorded in the distributed ledger to transfer ownership to a prescription service when the pharmacy is selected to dispense the prescription. In some embodiments, when a submission is received, a submission token transaction is recorded in the distributed ledger that transfers ownership of the submission token from the pharmacy to the prescription transaction. In some embodiments, after receiving the indication that the patient has selected a dispensing pharmacy, for each pharmacy not selected to dispense the prescription, a submission token transaction that transfers ownership of the submission token back to the pharmacy is recorded in the distributed ledger and for the pharmacy selected to dispense the prescription, a submission token that transfers ownership of the submission token to a prescription service is recorded in the distributed ledger. In some embodiments, a submission identifies a price and an incentive for selection of the pharmacy.

In some embodiments, a method performed by one or more computing systems for tracking prescriptions is provided. The method records in a blockchain a prescription transaction that identifies a prescription and a patient. The method records in the blockchain a submission selection transaction for controlling selection of a pharmacy to dispense the prescription. For each of a plurality of pharmacies, the method records in the blockchain a submission transaction with submission information relating to dispensing of the prescription by the pharmacy. The method records in the blockchain an indication of a pharmacy selected to dispense the prescription. The method records in the blockchain a dispense transaction indicating that the selected pharmacy has dispensed the prescription. In some embodiments, prior to selection of the pharmacy to dispense the prescription, for each of the plurality of pharmacies, the method records in the blockchain a submission token transaction that transfers ownership of a submission token from the pharmacy to another entity. After selection of the pharmacy to dispense the prescription, for each of the pharmacies not selected, the method records in the blockchain a submission token transaction that transfers ownership of a submission token from the other entity to the pharmacy. In some embodiments, for each dosage of the prescription, the method records in the blockchain a dose token transaction to create a dose token that is owned by an entity other than the patient. In some embodiments, the dose token transactions are recorded when the prescription is dispensed. In some embodiments, when the patient indicates that a dose has been taken, the method records in the blockchain a dose token transaction to transfer ownership of a dose token to the patient from the entity. In some embodiments, prior to recording in the blockchain the dose token transaction to transfer ownership of the dose token, the method confirms that the dose is for the prescription. In some embodiments, when dosage circuitry associated with a dose indicates that a dose has been taken, the method records in the blockchain a dose token transaction to transfer ownership of a dose token to the patient from the other party. In some embodiments, the dosage circuitry is a component of a device for administering a dose. In some embodiments, the dosage circuitry is included with a dose that is ingested. In some embodiments, prior to recording the prescription transaction, the method validates the prescription to ensure that the prescription is valid for the patient. In some embodiments, prior to recording the dispense transaction, the method validates the prescription to ensure that the prescription complies with rules implemented by a smart contract of the prescription transaction. In some embodiments, prior to recording the prescription transaction, the method determines whether the prescription complies with formulary information for the patient. In some embodiments, prior to recording the dispense transaction, the method determines whether the prescription complies with formulary information for the patient. In some embodiments, the recording in the blockchain of the indication of a pharmacy selected to dispense the prescription includes recording in the blockchain a selected submission transaction. In some embodiments, when the submission information for the pharmacy selected to dispense the prescription includes an incentive, the method records in the blockchain an incentive transaction indicating that the patient is owner of an incentive token for the incentive. In some embodiments, the submission information for a pharmacy is generated by applying rules specific to the pharmacy. In some embodiments, the submission information for a pharmacy is collected by sending to a system of the pharmacy the prescription and patient information and receiving from the system of the pharmacy the submission information.

In some embodiments, a method performed by one or more computing systems for monitoring a prescription is provided. The method displays prescription information relating to a prescription. For each of a plurality of pharmacies, the method displays submission information for the pharmacy relating to dispensing the prescription. The method receives from a patient selection of a pharmacy to dispense the prescription wherein a prescription transaction relating to the prescription is recorded in a blockchain. After the prescription is dispensed by the selected pharmacy, the method receives from the patient an indication that a dose was taken wherein a dose token transaction is recorded in the blockchain. In some embodiments, the method receives from the patient an indication to reject the prescription. In some embodiments, after the patient rejects the prescription, the method displays prescription information for a different prescription. In some embodiments, the method receives from a system of a prescriber the prescription information. In some embodiments, the prescription information specifies an incentive. In some embodiments, a dispense transaction is recorded in the blockchain when the prescription is dispensed by the selected pharmacy. In some embodiments, when the prescription is dispensed, a dose token transaction is recorded in the blockchain for each dose of the prescription with an entity as owner of a dose token. In some embodiments, when a dose is taken, a dose token transaction is recorded in the blockchain to transfer ownership of the dose token from the entity to the patient.

In some embodiments, one or more computer-readable storage mediums storing a blockchain are provided. The blockchain includes a prescription transaction that includes prescription information for a prescription. The blockchain includes a submission selection transaction with code for coordinating selection of a pharmacy to dispense the prescription. For each of a plurality of pharmacies, the blockchain includes a submission transaction with submission information relating to dispensing the prescription. The blockchain includes a dispense transaction indicating that a selected pharmacy has dispensed the prescription. For each dose of the prescription, the blockchain includes a dose token transaction indicating that an entity is owner of a dose token for the dose. In some embodiments, the blockchain includes a selected submission transaction indicating a pharmacy selected to dispense the prescription. In some embodiments, the blockchain includes a dose token transaction that transfers ownership of a dose transaction from the entity to a patient. In some embodiments, the blockchain includes, for each pharmacy, a submission token transaction that transfers ownership of a submission token from the pharmacy to an entity. In some embodiments, the blockchain includes, for each pharmacy not selected to dispense the prescription, a submission token transaction that transfers ownership of a submission token from the entity to the pharmacy. In some embodiments, the blockchain includes, for the pharmacy that is selected to dispense the prescription, a submission token transaction that transfers ownership of a submission token from the entity to a prescription service. In some embodiments, the blockchain includes an incentive token transaction with the patient as owner of an incentive token created by the pharmacy selected to dispense the prescription.

In some embodiments, one or more computing systems for tracking prescriptions are provided. The one or more computing systems includes one or more computer-readable storage mediums storing computer-executable instructions and one or more processors for executing the computer-executable instructions stored in the one or more computer-readable storage mediums. The instructions control the one or more computing systems to record in a blockchain a prescription transaction that identifies a prescription and a patient. The instructions control the one or more computing systems to record in the blockchain a submission selection transaction for controlling selection of a pharmacy to dispense the prescription. The instructions control the one or more computing systems to record in the blockchain a dispense transaction indicating that the pharmacy has dispensed the prescription. The instructions control the one or more computing systems, for each dose of the prescription, record in the blockchain a dose token transaction representing a dose token. In some embodiments, the computer-executable instructions further control the one or more computing systems to record in the blockchain an indication of a pharmacy selected to dispense the prescription and, for each of a plurality of pharmacies, record in the blockchain a submission transaction with submission information relating to dispensing of the prescription by the pharmacy. In some embodiments, the computer-executable instructions further control the one or more computing systems to prior to selection of the pharmacy to dispense the prescription, for each of the plurality of pharmacies, record in the blockchain a submission token transaction that transfers ownership of a submission token from the pharmacy to an entity and after selection of the pharmacy to dispense the prescription, for each of the pharmacies not selected, record in the blockchain a submission token transaction that transfers ownership of a submission token from the entity to the pharmacy. In some embodiments, the computer-executable instructions further control the one or more computing systems to, for each dosage of the prescription, record in the blockchain a dose token transaction to transfer ownership of a dose token from the entity to the patient.

Although the subject matter has been described in language specific to structural features and/or acts, it is to be understood that the subject matter defined in the appended claims is not necessarily limited to the specific features or acts described above. Rather, the specific features and acts described above are disclosed as example forms of implementing the claims. Accordingly, the invention is not limited except as by the appended claims.

The invention claimed is:

1. A method performed by one or more computing systems for selecting a pharmacy for dispensing a prescription prescribed by a prescriber, the method comprising:

prior to selection of a pharmacy to dispense the prescription,
under control of a prescriber computing system of the prescriber:
receiving an indication of the prescription that identifies a patient and prescription details;
recording in a distributed ledger a prescription transaction for the patient, the prescription transaction including a prescription selection smart contract that records in the distributed ledger a submission selection transaction with a submission selection smart contract that controls the selecting of the pharmacy for dispensing the prescription, the prescription transaction indicating a prescription for which a pharmacy has not been selected to dispense the prescription, the prescription transaction identifying the patient and prescription details, including an identifier of the prescriber based on a public key of the prescriber, and being digitally signed using a private key of the prescriber;

for each of a plurality of pharmacies,
under control of a pharmacy computing system of the pharmacy:
receiving a submission for dispensing the prescription, the submission indicating that the pharmacy is available to dispense the prescription; and
recording in the distributed ledger a submission transaction indicating that the pharmacy is available to dispense the prescription, the submission transaction including an identifier of the pharmacy based on a public key of the pharmacy and being digitally signed using a private key of the pharmacy; and under control of a patient computing system of the patient:

receiving an indication that the patient has selected one of the plurality of pharmacies as a dispensing pharmacy to dispense the prescription based on the submissions; and sending to the submission selection transaction an indication of the dispensing pharmacy wherein upon receiving the indication of the dispensing pharmacy, the submission selection smart contract records in the distributed ledger a selected submission transaction indicating the dispensing pharmacy, the submission selection including an identifier of the patient based on a public key of the patient and being digitally signed using a private key of the patient.

2. The method of claim 1 wherein, for each submission of a pharmacy, a submission token transaction is recorded in the distributed ledger to transfer ownership to a prescription service when the pharmacy is selected to dispense the prescription.

3. The method of claim 2 wherein when a submission is received, a submission token transaction is recorded in the distributed ledger that transfers ownership of the submission token from the pharmacy to the prescription transaction.

4. The method of claim 3 wherein after receiving the indication that the patient has selected a dispensing pharmacy:

for each pharmacy not selected to dispense the prescription, a submission token transaction that transfers ownership of the submission token back to the pharmacy is recorded in the distributed ledger; and for the pharmacy selected to dispense the prescription, a submission token that transfers ownership of the submission token to a prescription service is recorded in the distributed ledger.

5. The method of claim 1 wherein a submission identifies a price and an incentive for selection of the pharmacy.

6. A method performed by one or more computing systems for tracking prescriptions, the method comprising:

under control of a prescriber computing system of the prescriber, recording in a blockchain a prescription transaction that identifies a prescription and a patient, the prescription transaction including a prescription selection smart contract and including an identifier of the prescriber based on a public key of the prescriber, and being digitally signed using a private key of the prescriber;

under control of the prescription transaction smart contract, recording in the blockchain a submission selection transaction for controlling selection of a pharmacy to dispense the prescription, the submission selection transaction including a submission selection smart contract;

under control each of a plurality of pharmacy computing systems of pharmacies, recording in the blockchain a submission transaction with submission information relating to dispensing of the prescription by the pharmacy, the submission transaction including a reference to the prescription transaction and including an identifier of the pharmacy based on a public key of the pharmacy and being digitally signed using a private key of the pharmacy;

under control of the submission selection transaction, receiving from a patient computing system of the patient an indication of a pharmacy selected to dispense the prescription;

recording in the blockchain an indication of the selected pharmacy; and notifying the selected pharmacy of the selection;

under control of the pharmacy computing system of the selected pharmacy, recording in the blockchain a dispense transaction indicating that the selected pharmacy has dispensed the prescription and including the identifier of the selected pharmacy based on the public key of the selected pharmacy and being digitally signed using the private key of the selected pharmacy.

7. The method of claim 6 further comprising:

prior to selection of the pharmacy to dispense the prescription, for each of the plurality of pharmacies, recording in the blockchain a submission token transaction that transfers ownership of a submission token from the pharmacy to another entity; and after selection of the pharmacy to dispense the prescription, for each of the pharmacies not selected, recording in the blockchain a submission token transaction that transfers ownership of a submission token from the other entity to the pharmacy.

8. The method of claim 6 further comprising, for each dosage of the prescription, recording in the blockchain a dose token transaction to create a dose token that is owned by an entity other than the patient.

9. The method of claim 8 wherein the dose token transactions are recorded when the prescription is dispensed.

10. The method of claim 8 wherein when the patient indicates that a dose has been taken, recording in the blockchain a dose token transaction to transfer ownership of a dose token to the patient from the entity.

11. The method of claim 10 further comprising prior to recording in the blockchain the dose token transaction to transfer ownership of the dose token, confirming that the dose is for the prescription.

12. The method of claim 8 wherein when dosage circuitry associated with a dose indicates that a dose has been taken, recording in the blockchain a dose token transaction to transfer ownership of a dose token to the patient from the other party.

13. The method of claim 12 wherein the dosage circuitry is a component of a device for administering a dose.

14. The method of claim 12 wherein the dosage circuitry is included with a dose that is ingested.

15. The method of claim 6 further comprising, prior to recording the prescription transaction, validating the prescription to ensure that the prescription is valid for the patient.

16. The method of claim 6 further comprising, prior to recording the dispense transaction, validating the prescription to ensure that the prescription complies with rules implemented by a smart contract of the prescription transaction.

17. The method of claim 6 further comprising, prior to recording the prescription transaction, determining whether the prescription complies with formulary information for the patient.

18. The method of claim 6 further comprising, prior to recording the dispense transaction, determining whether the prescription complies with formulary information for the patient.

19. The method of claim 6 wherein the recording in the blockchain of the indication of a pharmacy selected to dispense the prescription includes recording in the blockchain a selected submission transaction.

20. The method of claim 19 wherein when the submission information for the pharmacy selected to dispense the prescription includes an incentive, further comprising recording in the blockchain an incentive transaction indicating that the patient is owner of an incentive token for the incentive.

21. The method of claim 6 wherein the submission information for a pharmacy is generated by applying rules specific to the pharmacy.

22. The method of claim 6 wherein the submission information for a pharmacy is collected by sending to a system of the pharmacy the prescription and patient information and receiving from the system of the pharmacy the submission information.

23. The method of claim 1 wherein the prescription selection smart contract sends to the patient a notification of the prescription and the submission selection smart contract sends to the pharmacy computer system of the dispensing pharmacy a notification that the dispensing pharmacy has been selected to dispense the prescription.

24. The method of claim 1 wherein the distributed ledger is a blockchain.

25. A method performed by one or more computing systems for tracking prescriptions via a blockchain, the method comprising:
under control of a prescriber computing system of a prescriber,
generating a prescription transaction that identifies a prescription, a prescriber, a patient, and a prescription selection smart contract, the prescriber identified based on a public key of the prescriber,
signing the prescription transaction with a private key of the prescriber, and
sending via a communication channel the signed prescription transaction to nodes of the blockchain for storing the signed prescription transaction in a replica of the blockchain maintained by each node;
under control of the prescription transaction smart contract,
generating a submission selection transaction that identifies a submission selection smart contract that controls selection of a pharmacy to dispense the prescription, and
sending via a communication channel the submission selection transaction to nodes of the blockchain for storing the submission selection transaction in the replica of the blockchain maintained by each node;
under control each of a plurality of pharmacy computing systems of pharmacies,
generating a submission transaction with submission information relating to dispensing of the prescription by the pharmacy and including a reference to the prescription transaction and an identifier of the pharmacy based on a public key of the pharmacy,
signing the submission transaction with a private key of the pharmacy, and
sending via a communication channel the signed submission transaction to nodes of the blockchain for storing the signed submission transaction in the replica of the blockchain maintained by each node;
under control of the submission selection smart contract,
receiving from a patient computing system of the patient an indication of a pharmacy selected to dispense the prescription,
recording in the blockchain an indication of the selected pharmacy, and
notifying the selected pharmacy of the selection; and
under control of the pharmacy computing system of the selected pharmacy,
generating a dispense transaction indicating that the selected pharmacy has dispensed the prescription and including an identifier based on a public key of the selected pharmacy,
signing the dispense transaction with a private key of the selected pharmacy, and
sending via a communication channel the signed dispense transaction to nodes of the blockchain for storing the signed dispense transaction in the replica of the blockchain maintained by each node.

* * * * *

UNITED STATES PATENT AND TRADEMARK OFFICE
CERTIFICATE OF CORRECTION

| | |
|---|---|
| PATENT NO. | : 11,393,568 B2 |
| APPLICATION NO. | : 15/855930 |
| DATED | : July 19, 2022 |
| INVENTOR(S) | : Blackley et al. |

It is certified that error appears in the above-identified patent and that said Letters Patent is hereby corrected as shown below:

In the Specification

Column 6, Line 25: "dose token changed until it is owned by a pharmacy."
Should read as: --dose token is changed until it is owned by a pharmacy.--

Column 6, Lines 35-36: "legal ownership, but rather may"
Should read as: --legal ownership but, rather, may--

Column 7, Line 56: "A pharmacy may also may offer"
Should read as: --A pharmacy may also offer--

Column 11, Lines 42-43: "drop-down list for as selecting the quantity of the medicine has been taken."
Should read as: --drop-down list for selecting the quantity of the medicine that has been taken.--

Column 12, Line 8: "(e.g., National Institute of"
Should read as: --(e.g., National Institutes of--

Column 12, Line 10: "provides the patient's prescriber"
Should read as: --provided by the patient's prescriber--

Column 12, Line 20: "Internet-of-Thing devices"
Should read as: --Internet-of-Things devices--

Column 12, Line 25: "of information using audio"
Should read as: --information using audio--

Column 12, Line 30: "various applications that of the client devices."
Should read as: --various applications of the client devices.--

Column 12, Line 34: "as the heath information"

Signed and Sealed this
Thirteenth Day of December, 2022

Katherine Kelly Vidal
*Director of the United States Patent and Trademark Office*

CERTIFICATE OF CORRECTION (continued)
U.S. Pat. No. 11,393,568 B2

Should read as: --as the health information--

Column 13, Line 1: "the patient is a physician's office"
Should read as: --the patient is in a physician's office--

Column 14, Line 1: "system may write prescription"
Should read as: --system may write a prescription--

Column 14, Line 15: "(e.g. Bitcoin)."
Should read as: --(e.g., Bitcoin).--

Column 15, Line 30: "to the participant."
Should read as: --of the participant.--

Column 15, Line 37: "global positioning system"
Should read as: --Global Positioning System--

Column 16, Lines 4-5: "or field programmable"
Should read as: --or field-programmable--

Column 17, Line 26: "is invoked passing submissions"
Should read as: --is invoked, passing submissions--

Column 17, Line 49: "block 903."
Should read as: --decision block 903.--

Column 19, Lines 1-2: "that seem to fraudulent,"
Should read as: --that seems to be fraudulent,--

Column 22, Line 4: "record in the blockchain"
Should read: --to record in the blockchain--

Column 22, Line 13: "computing systems to prior"
Should read as: --computing systems to record, prior--

Column 22, Line 15: "pharmacies, record in the blockchain"
Should read as: --pharmacies, in the blockchain--

Column 22, Line 17: "pharmacy to an entity"
Should read as: --pharmacy to an entity,--

In the Claims

Column 23, Line 17: "selection including an identifier"
Should read as: --selection transaction including an identifier--
Column 23, Line 27: "ownership of the submission"

CERTIFICATE OF CORRECTION (continued)
U.S. Pat. No. 11,393,568 B2

Should read as: --ownership of a submission--

Column 24, Line 6: "of the selection;"
Should read as: --of the selection; and--

Column 25, Line 19: "pharmacy computer system"
Should read as: --pharmacy computing system--